US008969297B2

(12) United States Patent
Katz

(10) Patent No.: US 8,969,297 B2
(45) Date of Patent: Mar. 3, 2015

(54) METHODS AND COMPOSITIONS FOR THE INDUCTION OF HYPOTHERMIA

(75) Inventor: Laurence M. Katz, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 202 days.

(21) Appl. No.: 13/377,257

(22) PCT Filed: Jun. 9, 2010

(86) PCT No.: PCT/US2010/037908
§ 371 (c)(1),
(2), (4) Date: Feb. 20, 2012

(87) PCT Pub. No.: WO2010/144535
PCT Pub. Date: Dec. 16, 2010

(65) Prior Publication Data
US 2012/0282227 A1 Nov. 8, 2012

Related U.S. Application Data

(60) Provisional application No. 61/185,825, filed on Jun. 10, 2009.

(51) Int. Cl.
*A61K 35/12* (2006.01)
*A61K 38/11* (2006.01)
*A61K 38/28* (2006.01)
*A61P 9/10* (2006.01)
*A61P 9/00* (2006.01)
*A61P 25/00* (2006.01)
*A61K 31/045* (2006.01)
*A61K 31/167* (2006.01)
*A61K 31/395* (2006.01)

(52) U.S. Cl.
CPC ............ *A61K 31/045* (2013.01); *A61K 31/167* (2013.01); *A61K 31/395* (2013.01); *Y10S 514/807* (2013.01)
USPC ............... 514/10.9; 514/6.5; 514/1; 514/807; 514/724; 514/740; 514/741

(58) Field of Classification Search
None
See application file for complete search history.

(56) References Cited

U.S. PATENT DOCUMENTS 5,453,445 A * 9/1995 Henry ........................... 514/626
7,319,090 B2 1/2008 Katz
2002/0095144 A1 7/2002 Carl
2004/0102368 A1 5/2004 Katz

FOREIGN PATENT DOCUMENTS

DE 103 33 240 A1 2/2005

OTHER PUBLICATIONS

Zimmerman, Janice L.; "Hypothermia, Hyperthermia, and Rhabdomyolysis" ACCP/SCCM Combined Critical Care Course, Orlando 321-332, 1999.*
Steiner, Alexandre A.; et al; "Role of nitric oxide in systemic vasopressin-induced hypothermia" American Journal of Physiology—Regulatory, Integrative and Comparative Physiology, 275, R937-R941, 1998.*
Jatana, Manu; et al; "Combination of Systemic Hypothermia and N-acetylcysteine Attenuates Hypoxic-Ischemic Brain Injury in Neonatal Rats" Pediatric Research, 59, 684-689, 2006.*
Halsted, Charles H.; et al; "Folate deficiency disturbs hepatic methionine metabolism and promotes liver injury in the ethanol-fed micropig" Proceedings of the National Academy of Sciences, 99, 10072-10077, 2002.*
Bernard, Stephen A.; et al; "Induced hypothermia in critical care medicine" Critical Care Medicine, 31, 2041-2051, 2003.*
Aronowski, J., et al., "Ethanol Plus Caffeine (Caffeinol) for Treatment of Ischemic Stroke—Preclinical Experience," *Stroke*, 2003, vol. 34(1), pp. 1246-1251.
Friedman, H., et al., "Acute Effects of Ethanol on Myocardial Blood Flow in the Nonischemic and Ischemic Heart," *The American Journal of Cardiology*, 1981, vol. 47(1), pp. 61-67.
Kransingh, S., "Therapeutic hypothermia," University of Kwazulu-Natal, Department of Anaesthetics, 2008, 8 pages, retrieved from the Internet: URL:http://anaesthetics.ukzn.ac.za/Uploads/5b73f4a6-9181-42c2-90e0-c316344ad4c7/
Therapeutic%20hypothermia%20%20%20Dr%20Kransingh.pdf.
Luttinger, D., et al., "Enhancement of Ethanol-induced Sedation and Hypothermia by Centrally Administered Neurotensin, β-Endorphin and Bombesin," *Neuropharmacology*, 1981, vol. 20(3), pp. 305-309.
Turnipseed, W., et al., "Hemodynamic Effects of Intravenous Alcohol on Patients with Ischemic Limb Disease," *Journal of Surgical Research*, 1976, vol. 20(5), pp. 477-480.

(Continued)

*Primary Examiner* — Blaine Lankford
*Assistant Examiner* — David Berke-Schlessel
(74) *Attorney, Agent, or Firm* — Alston & Bird LLP

(57) ABSTRACT

Provided herein are methods for the induction of hypothermia and the treatment of clinical insults in a subject through the administration of a regulated hypothermic multidrug combination. The compositions or multidrug combinations of the invention comprise a regulated hypothermic compound or a dopamine receptor agonist; a vasoactive compound; and an antiarrhythmic compound or a serotonin 5-HT3 receptor antagonist. Additional agents can be included in the composition including at least one of an antioxidant, a vitamin, N-acetylcysteine, and an antihyperglycemic compound. The invention further recognizes that a two phase delivery of multidrug combinations, a rapid infusion of the composition to induce hypothermia followed by a period of slow infusion to maintain the hypothermic state for a sustained period of time. Using the two phase delivery method of the invention, the composition may comprise ethanol and, optionally, at least one of a vasoactive compound, an antiarrhythmic compound, a serotonin 5-HT3 receptor antagonist, an antioxidant, a vitamin, N-acetylcysteine, and an antihyperglycemic compound. This two phase delivery method can be used to deliver any of the compositions of the invention and provides significant benefits to a patient.

26 Claims, 1 Drawing Sheet

(56) References Cited

OTHER PUBLICATIONS

"Mild Therapeutic Hypothermia to Improve the Neurologic Outcome After Cardiac Arrest," *The New England Journal of Medicine*, 2002, vol. 346(8), pp. 549-556.
Altura, B., et al., "Symposium on Cardiovascular Effects of Ethanol—Part II: Peripheral and Cerebrovascular Actions of Ethanol, Acetaldehyde, and Acetate: Relationship to Divalent Cations," *Alcoholism Clinical and Experimental Research*, 1987, vol. 11(2), pp. 99-111.
Aranowski, J., et al., "Ethanol Plus Caffeine (Caffeinol) for Treatment of Ischemic Stroke: Preclinical Experience," *Stroke*, 2003, vol. 34, pp. 1246-1251.
Arrich, J., et al., "Clinical application of mild therapeutic hypothermia after cardiac arrest," *Crit Care Med*, 2007, vol. 35(4), pp. 1041-1047.
Asano, M., et al., "Optimal Temperature of Continuous Lidocaine Perfusion for the Heart Preservation," *The Japanese Journal of Thoracic and Cardiovascular Surgery*, 2003, vol. 51(1), pp. 1-9.
Bar-Joseph, G., et al., Clinical use of sodium bicarbonate during cardiopulmonary resuscitation—is it used sensibly? *Resuscitation*, 2002, vol. 54, pp. 47-55.
Belayev, L., et al., "Caffeinol confers cortical but not subcortical neuroprotection after transient focal cerebral ischemia in rats," *Brain Research*, 2004, vol. 1008, pp. 278-283.
Bernard, S., et al., "Treatment of Comatose Survivors of Out-of-Hospital Cardiac Arrest With Induced Hypothermia," *N Engl J Med*, 2002, vol. 346(8), pp. 557-563.
Bernard, S., et al., "Induced hypothermia using large volume, ice-cold intravenous fluid in comatose survivors of out-of-hospital cardiac arrest; a preliminary report," *Resuscitation*, 2003, vol. 56, pp. 9-13.
Bernard, Stephen, "Hypothermia after cardiac arrest: How to cool and for how long?" *Crit Care Med*, 2004, vol. 32(3), pp. 897-899.
Bhattacharya, P., et al., "Post Anaesthesia Shivering (PAS): A Review," *Indian J. Anaesth.*, 2003, vol. 47(2), pp. 88-93.
Brown, C., et al., "A Comparison of Standard-Dose and High-Dose Epinephrine in Cardiac Arrest Outside the Hospital," *N Engl J Med*, 1992, vol. 327(15), pp. 1051-1055.
Busto, R., et al., "The Importance of Brain Temperature in Cerebral Ischemic Injury," *Stroke*, 1989, vol. 20, pp. 1113-1114.
Calabrese, V., et al., "HSP70 Induction in the Brain Following Ethanol Administration in the Rat: Regulation by Glutathione Redox State," *Biochemical and Biophysical Research Communications*, 2000, vol. 269, pp. 397-400.
Clifton, Guy L., "Is keeping cool still hot? An update on hypothermia in brain injury," *Current Opinion in Critical Care*, 2004, vol. 10, pp. 116-119.
Cloyd, J., et al., "Epidemiological and medical aspects of epilepsy in the elderly," *Epilepsy Research*, 2006, vol. 68S, pp. S39-S48.
Colquitt, M., et al., "Drunk Drivers and Medical and Social Injury," *The New England Journal of Medicine*, 1987, vol. 317, pp. 1262-1266.
Crews, F., et al., "Ethanol, Stroke, Brain Damage, and Excitotoxicty," *Pharmacology Biochemistry and Behavior*, 1998, vol. 59(4), pp. 981-991.
Crossley, A. W. A., "Pen-operative shivering," *Anaesthesia*, 1992, vol. 47(3), pp. 193-195.
Danysz, W., et al., "Involvement of NMDA Receptors in Acute and Chronic Effects of Ethanol," *Alcohol and Experimental Research*, 1992, vol. 16(3), pp. 499-504.
Dash, P., et al., "Post-Trauma Administration of Caffeine Plus Ethanol Reduces Contusion Volume and Improves Working Memory in Rats," *Journal of Neurotrauma*, 2004, vol. 21(11), pp. 1573-1583.
D'Cruz, B., et al., "Hypothermic Reperfusion After Cardiac Arrest Augments Brain-Derived Neurotrophic Factor Activation," *Journal of Cerebral Blood Flow & Metabolism*, 2002, vol. 22, pp. 843-851.
Deitrich, R., et al., "Oxidation of Ethanol in the Brain and Its Consequences," *Alcohol Research & Health*, 2006, vol. 29(4), pp. 266-273.
Delin, C., et al., "Drinking and the Brain: Current Evidence," *Alcohol and Alcoholism*, 1992, vol. 27(2), pp. 117-126.
Diamant, M., et al., "Differential effects of centrally injected AVP on heart rate, core temperature, and behavior in rats," *Am J Physiol (Regulatory Integrative Comp Physiol)*, 1993, vol. 264, pp. R51-R61.
Dietrich W., et al., "Hyperthermia and central nervous system injury," *Progress in Brain Research*, 2007, vol. 162, pp. 201-217.
Dinh, T., et al., "Effect of Body Temperature on Acute Ethanol Toxicity," *Life Sciences*, 1979, vol. 25, pp. 547-552.
Drago, F., et al., "The Block of Central Vasopressin $V_1$ but not $V_2$ Receptors Suppresses Grooming Behavior and Hypothermia Induced by Intracerebroventricular Vasopressin in Male Rats," *Peptides*, 1997, vol. 18(9), pp. 1389-1392.
Drew, K., et al., "Central nervous system regulation of mammalian hibernation: implications for metabolic suppression and ischemia tolerance," *Journal of Neurochemistry*, 2007, vol. 102, pp. 1713-1726.
Eberhart, L., et al., "Independent Risk Factors for Postoperative Shivering," *Anesth Analg*, 2005, vol. 101, pp. 1849-1857.
Eisenberg, M., et al., "Cardiac Resuscitation," *N Engl J Med*, 2001, vol. 344(17), pp. 1304-1313.
Enache, M., et al., "Impact of an acute exposure to ethanol on the oxidative stress status in the hippocampus of prenatal restraint stress adolescent male rats," *Brain Research*, 2008, vol. 1191, pp. 55-62.
Falk, Bareket, "Effects of Thermal Stress During Rest and Exercise in the Paediatric Population," *Sports Med*, 1998, vol. 25(4), pp. 221-240.
Finn, D., et al., "Body Temperature Influences Ethanol and Ethanol/Pentobarbital Lethality in Mice," *Alcohol*, 1991, vol. 8, pp. 39-41.
Fischer, W., "Influence of ethanol on the threshold for electroshock-induced seizures and electrically-evoked hippocampal afterdischarges," *J Neural Transm*, 2005, vol. 112, pp. 1149-1163.
Frank, S., et al., "The Catecholamine, Cortisol, and Hemodynamic Responses to Mild Perioperative Hypothermia," *Anesthesiology*, 1995, vol. 82, pp. 83-93.
Frank, S., et al., "Adrenergic, respiratory, and cardiovascular effects of core cooling in humans," *Am J Physiol.*, 1997, vol. 272, pp. R557-R562.
Froehlich, J., et al., "Induction of Steady-State Blood Alcohol Levels: Application to the Study of Within-Session Alcohol Tolerance in Rats," *Alcoholism: Clinical and Experimental Research*, 2001, vol. 25(3), pp. 370-376.
Ginsberg, Myron D., "Adventures in the Pathophysiology of Brain Ischemia: Penumbra, Gene Expression, Neuroprotection: The 2002 Thomas Willis Lecture," *Stroke*, 2003, vol. 34, pp. 214-223.
Gluckman, P., et al., "Selective head cooling with mild systemic hypothermia after neonatal encephalopathy: multicentre randomised trial," *Lancet*, 2005, vol. 365, pp. 663-670.
Gordon, Christopher J., "A Review of Terms for Regulated Vs. Forced, Neurochemical Cal-Induced Changes in Body Temperature," *Life Sciences*, 1983, vol. 32, pp. 1285-1295.
Gordon, Christopher J., "Relationship Between Autonomic and Behavioral Thermoregulation in the Mouse," *Physiology & Behavior*, 1985, vol. 34, pp. 687-690.
Gordon C., et al., "Effect of Alcohol on Behavioral and Autonomic Thermoregulation in Mice," *Alcohol*, 1986, vol. 3, pp. 339-343.
Gordon, C., et al., "Behavioral Thermoregulation in the Rat Following the Oral Administration of Ethanol," *Alcohol & Alcoholism*, 1988, vol. 23(5), pp. 383-390.
Gordon, C., et al., "Effect of Ethyl Alcohol on Thermoregulation in Mice Following the Induction of Hypothermia or Hyperthermia," *Pharmacology Biochemistry & Behavior*, 1988, vol. 29, pp. 693-698.
Gordon, C., et al., "Thermoregulation at a High Ambient Temperature Following the Oral Administration of Ethanol in the Rat," *Alcohol*, 1990, vol. 7, pp. 551-555.
Gordon, C., et al., "Thermoregulatory Response to Chemical Toxicants and Other Insults: Extrapolation from Experimental Animal to Human," *Ann N Y Acad Sci*, 1997, vol. 813, pp. 835-848.
Gordon, Christopher J., "The therapeutic potential of regulated hypothermia," *Emerg Med J*, 2001, vol. 18, pp. 81-89.
Gordon, C., et al., "Neurotensin analog NT77 induces regulated hypothermia in the rat," *Life Sciences*, 2003, vol. 73, pp. 2611-2623.

(56) References Cited

OTHER PUBLICATIONS

Gordon, C., et al., *Temperature and Toxicology: An Integrative, Comparative, and Environmental Approach*, 2005, Vol. CRC Press, Boca Raton, pp. 87-88.
Green, A. R., "Pharmacological approaches to acute ischaemic stroke: reperfusion certainly, neuroprotection possibly," *British Journal of Pharmacology*, 2008, vol. 153, pp. S325-S338.
Green, Robert, "The management of severe toxic alcohol ingestions at a tertiary care center after the introduction of fomepizole," *American Journal of Emergency Medicine*, 2007, vol. 25, pp. 799-803.
Greer, D., et al., "Impact of Fever on Outcome in Patients With Stroke and Neurologic Injury: A Comprehensive Meta-Analysis," *Stroke*, 2008, vol. 39, pp. 3029-3035.
Gueugniaud, P-Y, et al., "Vasopressin and Epinephrine vs. Epinephrine Alone in Cardiopulmonary Resuscitation," *N Engl J Med*, 2008, vol. 359(1), pp. 21-30.
Haight, J., et al., "Failure of Thermoregulation in the Cold During Hypoglycaemia Induced by Exercise and Ethanol," *J. Physiol.*, 1973, vol. 229, pp. 87-97.
Hicdonmez, T., et al., "Neuroprotective Effects of *N*-acetylcysteine on Experimental Closed Head Trauma in Rats," *Neurochem Res*, 2006, vol. 31, pp. 473-481.
Hipólito, L., et al., "Brain Metabolism of Ethanol and Alcoholism: An Update," *Current Drug Metabolism*, 2007, vol. 8, pp. 716-727.
Hjeresen, D., et al., "The Role of Arginine Vasopressin in the Development of Tolerance to Ethanol in Normal and Brattleboro Rats," *Peptides*, 1988, vol. 9(Suppl. 1), pp. 193-200.
Hoedemaekers, C., et al., "Comparison of cooling methods to induce and maintain normo- and hypothermia in intensive care unit patients: a prospective intervention study," *Critical Care*, 2007, vol. 11(R91), pp. 1-9.
Huttunen, P., et al., "Ethanol-induced Hypothermia and Thermogenesis of Brown Adipose Tissue in the Rat," *Alcohol*, 1998, vol. 15(4), pp. 315-318.
Inoue, Y, et al., "Thermoregulatory responses of prepubertal boys and young men in changing temperature linearly from 28 to 15° C.," *Eur J Appl Physiol*, 1996, vol. 72, pp. 204-208.
Johnston, C., et al., "Alcohol lowers the vasoconstriction threshold in humans without affecting core cooling rate during mild cold exposure," *Eur J Appl Physiol*, 1996, vol. 74, pp. 293-295.
Jordan, J., et al., "Hypothermia: Comparing technology," *Journal of the Neurological Sciences*, 2007, vol. 261, pp. 35-38.
Kalant, H., et al., "Effects of Ethanol on Thermoregulation," *Pharmac. Ther.*, 1984, vol. 23, pp. 313-364.
Kämäräinen, A., et al., "Hypothermic preconditioning of donor organs prior to harvesting and ischaemia using ice-cold intravenous fluids," *Medical Hypotheses*, 2009, vol. 73, pp. 65-66.
Kandasamy, S. B., "Effect of Ondansetron and ICS 205-930 on Radiation-Induced Hypothermia in Rats," *Radiation Research*, 1997, vol. 147, pp. 741-746.
Katz, L., et al., "Outcome Model of Asphyxial Cardiac Arrest in Rats," *Journal of Cerebral Blood Flow and Metabolism*, 1995, vol. 15, pp. 1032-1039.
Katz, L., et al., "Glucose plus insulin infusion improves cerebral outcome after asphyxial cardiac arrest," *Neuroreport*, 1998, vol. 9(15), pp. 3363-3367.
Katz, L., et al., "Neurotensin Analog NT69L Induces Rapid and Prolonged Hypothermia after Hypoxic Ischemia," *Academic Emergency Medicine*, 2001, vol. 8(12), pp. 1115-1121.
Katz, L., et al., "Neurotensin-induced hypothermia improves neurologic outcome after hypoxic-ischemia," *Crit Care Med*, 2004, vol. 32(3), pp. 806-810.
Katz, L., et al., "Regulated hypothermia reduces brain oxidative stress after hypoxic-ischemia," *Brain Research*, 2004, vol. 1017, pp. 85-91.
Kim, F., et al., "Pilot Randomized Clinical Trial of Prehospital Induction of Mild Hypothermia in Out-of-Hospital Cardiac Arrest Patients With a Rapid Infusion of 4° C. Normal Saline," *Circulation*, 2007, vol. 115, pp. 3064-3070.

Kim, Y., et al., "Delayed Postischemic Hyperthermia in Awake Rats Worsens the Histopathological Outcome of Transient Focal Cerebral Ischemia," *Stroke*, 1996, vol. 27, pp. 2274-2280.
Komatsu, R., et al., "Ondansetron does not reduce the shivering threshold in healthy volunteers," *British Journal of Anaesthesia*, 2006, vol. 96(6), pp. 732-737.
Kuboyama, K., et al., "Delay in cooling negates the beneficial effect of mild resuscitative cerebral hypothermia after cardiac arrest in dogs: A prospective, randomized study," *Critical Care Medicine*, 1993, vol. 21(9), pp. 1348-1358.
Lai, C., et al., "The Role of Protein Kinase A in Acute Ethanol-Induced Neurobehavioral Actions in Rats," *Anesth Analg.*, 2007, vol. 105, pp. 89-96.
Leblanc, A., et al., "Acute Tolerance to Ethanol in the Rat," *Psychopharmacologia*, 1975, vol. 41, pp. 43-46.
Liao, S., et al., "Ethanol attenuates ischemic and hypoxic injury in rat brain and cultured neurons," *Neuroreport*, 2003, vol. 14(16), pp. 2089-2094.
Lomax, P., et al., "Ethanol-Induced Hypothermia in the Rat," *Pharmacology*, 1980, vol. 21, pp. 288-294.
Lomax, P., et al., "Cold Acclimation and Resistance to Ethanol-Induced Hypothermia," *European Journal of Pharmacology*, 1982, vol. 84, pp. 87-91.
Lovinger, D., et al., "Tonic for what ails us? high-affinity $GABA_A$ receptors and alcohol," *Alcohol*, 2007, vol. 41, pp. 139-143.
Martin, S., et al., "Alcohol, respiration, skin and body temperature during cold water immersion," *J Appl Physiol.: Respirat Environ Exercise Physiol*, 1977, vol. 43, pp. 211-215.
Meyerhoff, D., et al., "Health Risks of Chronic Moderate and Heavy Alcohol Consumption: How Much Is Too Much?" *Alcohol Clin Exp Res*, 2005, vol. 29(7), pp. 1334-1340.
Mohler, F., et al, "Hypothermic Effects of a Homologous Series of Short-Chain Alcohols in Rats," *Journal of Toxicology and Environmental Health*, 1991, vol. 32, pp. 129-139.
Moore, T., et al., "Core Temperature Cooling in Healthy Volunteers After Rapid Intravenous Infusion of Cold and Room Temperature Saline Solution," *Annals of Emergency Medicine*, 2008, vol. 51(2), pp. 153-159.
Mustonen, H., et al., "Ethanol induced NF-κB activation protects against cell injury in cultured rat gastric mucosal epithelium," *Am J Physiol Gastrointest Liver Physiol*, 2007, vol. 292, G1614-G1621.
Neumar, R., et al., "Epinephrine and sodium bicarbonate during CPR following asphyxial cardiac arrest in rats," *Resuscitation*, 1995, vol. 29, pp. 249-263.
Nishio, S, et al., "Ischemic tolerance in the rat neocortex following hypothermic preconditioning," *J Neurosurg*, 2000, vol. 93, pp. 845-851.
O'Keefe, J., et al., "Alcohol and Cardiovascular Health: The Razor-Sharp Double-Edged Sword," *J. Am. Coll. Cardiol.*, 2007, vol. 50, pp. 1009-1014.
Olsen, R., et al., "$GABA_A$ receptor subtypes: the "one glass of wine" receptors," *Alcohol*, 2007, vol. 41, pp. 201-209.
Paradis, N. et al., "High-Dose Adrenaline and Cardiac Arrest," *Lancet*, 1988, vol. 2(8613), p. 749.
Patrini, C., et al., "Effect of Acute and Chronic Ethanol Administration on the Transport of Thiamine From Plasma to Different Brain Regions of the Rat," *Alcohol & Alcoholism*, 1988, vol. 23(6), pp. 455-463.
Perondi, M., et al., "A Comparison of High-Dose and Standard-Dose Epinephrine in Children with Cardiac Arrest," *N Engl J Med*, 2004, vol. 350(17), pp. 1722-1730.
Pignataro, L., et al., "Alcohol Regulates Gene Expression in Neurons via Activation of Heat Shock Factor 1," *The Journal of Neuroscience*, 2007, vol. 27(47), pp. 12957-12966.
Piriyawat, P., et al., "Pilot Dose-Escalation Study of Caffeine Plus Ethanol (Caffeinol) in Acute Ischemic Stroke," *Stroke*, 2003, vol. 34, pp. 1242-1245.
Polderman, Kees H., "Induced hypothermia and fever control for prevention and treatment of neurological injuries," *Lancet*, 2008, vol. 371, pp. 1955-1969.
Radovsky, A., et al., "Ischemic Neurons in Rat Brains After 6, 8, or 10 Minutes of Transient Hypoxic Ischemia," *Toxicol Pathol*, 1997, vol. 25(5), pp. 500-505.

(56) References Cited

OTHER PUBLICATIONS

Reynolds, K., et al., "Alcohol Consumption and Risk of Stroke—A Meta-analysis," *JAMA*, 2003, vol. 289(5), pp. 579-588.

Risbo, A., et al., "Human Body Temperature and Controlled Cold Exposure during Moderate and Severe Experimental Alcohol-Intoxication," *Acta anaesth. scand.*, 1981, vol. 25, pp. 215-218.

Safar, Peter, "Cerebral resuscitation after cardiac arrest: a review," *Circulation*, 1986, vol. 74(suppl IV), pp. IV-138-IV-153.

Sandoval, D., et al., "Forebrain and hindbrain effects of ethanol on counterregulatory responses to hypoglycemia in conscious rats," *Metabolism Clinical and Experimental*, 2007, vol. 56, pp. 1623-1628.

Sekhon, B., et al., "N-Acetyl cysteine protects against injury in a rat model of focal cerebral ischemia," *Brain Research*, 2003, vol. 971, pp. 1-8.

Shankaran, S., et al., "Whole-Body Hypothermia for Neonates with Hypoxic-Ischemic Encephalopathy," *N Engl J Med*, 2005, vol. 353(15), pp. 1574-1584.

Sheng, H., et al., "Catalytic Antioxidants as Novel Pharmacologic Approaches to Treatment of Ischemic Brain Injury," *Drug News Perspect*, 2002, vol. 15(10), pp. 654-665.

Shuaib, A., et al., "NXY-059 for the Treatment of Acute Ischemic Stroke," *N Engl Journal of Medicine*, 2007, vol. 357(6), pp. 562-571.

Siesjö, B., et al., "Neurocytotoxicity: pharmacological implications," *Fundam Clin Pharmacol*, 1991, vol. 5, pp. 755-767.

Silbergleit, R., et al., "Lack of a neuroprotective effect from N-acetylcysteine after cardiac arrest and resuscitation in a canine model," *Resuscitation*, 1999, vol. 40, pp. 181-186.

Siler-Marsiglio, K., et al., "Effects of Acute Ethanol Exposure on Regulatory Mechanisms of Bcl-2-Associated Apoptosis Promoter, Bad, in Neonatal Rat Cerebellum: Differential Effects During Vulnerable and Resistant Developmental Periods," *Alcoholism: Clinical and Experimental Research*, 2006, vol. 30(6), pp. 1031-1038.

Strong, R., et al., "Combination of low dose ethanol and caffeine protects brain from damage produced by focal ischemia in rats," *Neuropharmacology*, 2000, vol. 39, pp. 515-522.

Thomale, U-W., et al., "The effect of N-acetylcysteine on post-traumatic changes after controlled cortical impact in rats," *Intensive Care Med*, 2006, vol. 32, pp. 149-155.

Thompson, Scott M., "Modulation of Inhibitory Synaptic Transmission in the Hippocampus," *Progress in Neurobiology*, 1994, vol. 42, pp. 575-609.

Tiainen, M., et al., "Cognitive and Neurophysiological Outcome of Cardiac Arrest Survivors Treated With Therapeutic Hypothermia," *Stroke*, 2007, vol. 38, pp. 2303-2308.

Tien, H., et al., "Association Between Alcohol and Mortality in Patients with Severe Traumatic Head Injury," *Arch Surg*, 2006, vol. 141, pp. 1185-1191.

Towne, Alan R., "Epidemiology and Outcomes of Status Epilepticus in the Elderly," *International Review of Neurobiology*, 2007, vol. 81, pp. 111-127.

Wang, Q., et al., "Ethanol preconditioning protects against ischemia/reperfusion-induced brain damage: Role of NADPH oxidase-derived ROS," *Free Radical Biology & Medicine*, 2007, vol. 43, pp. 1048-1060.

Warner, D., et al., "Oxidants, antioxidants and the ischemic brain," *The Journal of Experimental Biology*, 2004, vol. 207, pp. 3221-3231.

Weinberg, J., et al., "Comparison of Intravenous Ethanol Versus Diazepam for Alcohol Withdrawal Prophylaxis in the Trauma ICU: Results of a Randomized Trial," *The Journal of TRAUMA® Injury, Infection, and Critical Care*, 2008, vol. 64(1), pp. 99-104.

Wright, W., et al., "Postresuscitative Intensive Care: Neuroprotective Strategies after Cardiac Arrest," *Seminars in Neurology*, 2006, vol. 26(4), pp. 396-402.

Yang, Y., et al., "Regulated hypothermia in the hypothyroid rat induced by administration of propylthiouracil," *American Journal of Physiology*, 1997, vol. 272(5), pp. R1390-R1395.

Yang, Y-L, et al., "Possible Role of Vasopressin in the Thermoregulatory Response to Chlorpyrifos in the Rat," *Pharmacology & Toxicology*, 2002, vol. 90, pp. 311-316.

Yoda, T., et al., "Effects of alcohol on thermoregulation during mild heat exposure in humans," *Alcohol*, 2005, vol. 36, pp. 195-200.

Zhao, H., et al., "General versus specific actions of mild-moderate hypothermia in attenuating cerebral ischemic damage," *Journal of Cerebral Blood Flow & Metabolism*, 2007, vol. 27, pp. 1879-1894.

Zhao, H., et al., "Conditions of protection by hypothermia and effects on apoptotic pathways in a rat model of permanent middle cerebral artery occlusion," *J Neurosurg*, 2007, vol. 107, pp. 636-641.

Zhao, P., et al., "GABA and glycine are protective to mature but toxic to immature rat cortical neurons under hypoxia," *European Journal of Neuroscience*, 2005, vol. 22, pp. 289-300.

Zhao, X., et al., "Combining Insulin-Like Growth Factor Derivatives Plus Caffeinol Produces Robust Neuroprotection After Stroke in Rats," *Stroke*, 2005, vol. 36, pp. 129-134.

Zhu, P., et al., "Ethanol Potentiates GABAergic Synaptic Transmission in a Postsynaptic Neuron/Synaptic Bouton Preparation From Basolateral Amygdala," *J Neurophysiol*, 2006, vol. 96, pp. 433-441.

\* cited by examiner

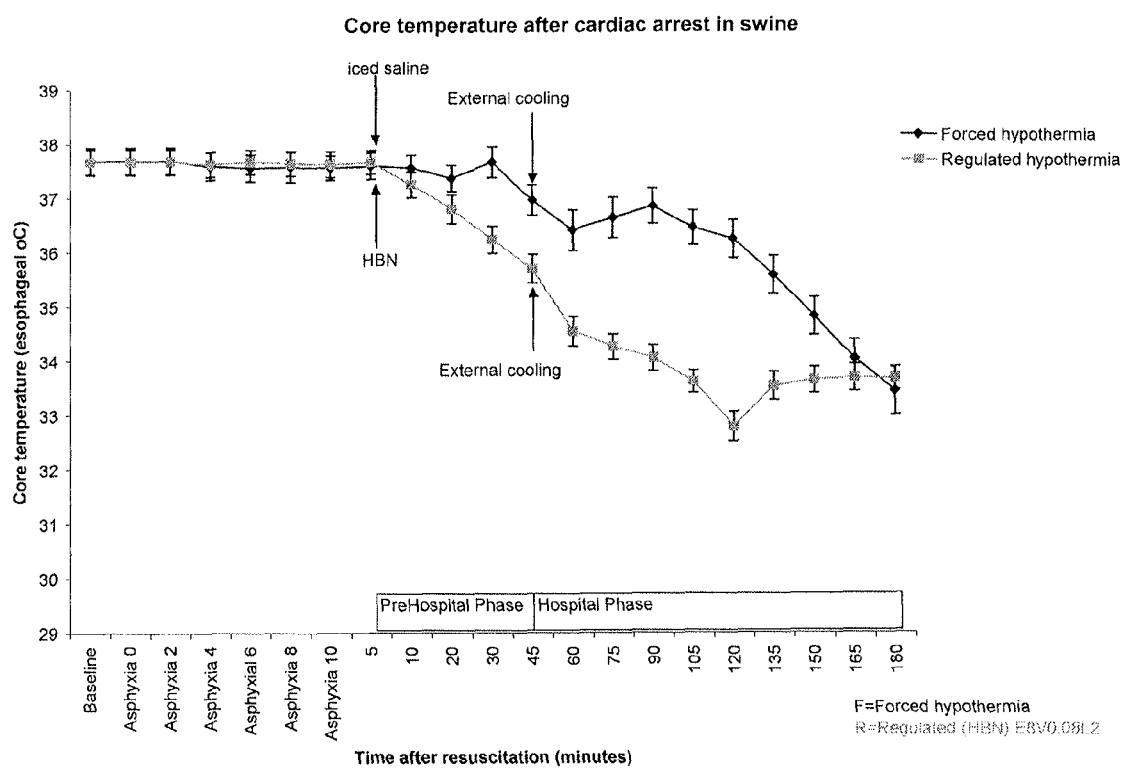

```
                          SEQUENCE LISTING

<160> NUMBER OF SEQ ID NOS: 2

<210> SEQ ID NO 1
<211> LENGTH: 13
<212> TYPE: PRT
<213> ORGANISM: Homo sapiens

<400> SEQUENCE: 1

Gln Leu Tyr Glu Asn Lys Pro Arg Arg Pro Tyr Ile Leu
1               5                   10

<210> SEQ ID NO 2
<211> LENGTH: 9
<212> TYPE: PRT
<213> ORGANISM: Homo sapiens

<400> SEQUENCE: 2

Cys Tyr Phe Gln Asn Cys Pro Arg Gly
1               5
```

METHODS AND COMPOSITIONS FOR THE INDUCTION OF HYPOTHERMIA

CROSS REFERENCE TO RELATED APPLICATIONS

This application is a U.S. National Stage Application based on PCT/US2010/037908, filed Jun. 9, 2010, which claims the benefit of U.S. Provisional Application No. 61/185,825, filed on Jun. 10, 2009, all of which are herein incorporated by reference in their entirety.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 412601SEQLIST.TXT, created on Dec. 8, 2011, and having a size of 657 bytes, and was filed in the Preliminary Amendment filed on Dec. 9, 2011. The sequence listing contained in this ASCII formatted document is part of the specification and is herein incorporated by reference in its entirety.

The official copy of the sequence listing is submitted electronically via EFS-Web as an ASCII formatted sequence listing with a file named 390112SEQLIST.txt, created on Jun. 9, 2010, and having a size of 4 KB and is filed concurrently with the specification. The sequence listing contained in this ASCII formatted document is part of the specification and is herein incorporated by reference in its entirety.

FIELD OF THE INVENTION

The present invention relates to the field of therapeutic hypothermia, particularly regulated hypothermia.

BACKGROUND OF THE INVENTION

Hypothermia is a condition of temperature-regulating organisms wherein the core body temperature becomes reduced below the normal range. Hypothermia has been used clinically for more than forty years to protect bodily organs from various pathophysiological insults, including ischemic insults such as cardiac arrest, hemorrhage, hypergravity, and hypoglycemia, and to reduce the toxicity of various drugs and environmental toxicants (see Gordon (2001) *Emerg Med J* 18:81-89). While the precise mechanisms responsible for the therapeutic effects of hypothermia are not fully understood, hypothermia causes a general reduction in cellular metabolism (Polderman (2008) *Lancet* 371:1955-1969). This reduction in cellular metabolism during hypothermia is especially beneficial to highly aerobic organs, such as the brain and heart, under ischemic conditions because it leads to a reduction in the demand for oxygen.

Currently, forced hypothermic methods are used for therapeutic hypothermia. Forced hypothermia involves the use of external and/or endovascular cooling methods to extract heat from the body to reduce the body temperature below the normal set-point temperature. External cooling methods consist of immersion of a subject in a cool bath or application of blankets or pads with cooled water circulating through channels in the walls of the blanket or pad to the skin of a subject. Other external methods include wetting of the skin or hair of the subject, cooling the air surrounding the subject, and blowing air across the subject's skin. Endovascular cooling generally involves the intravenous administration of a cool saline solution.

To combat the lowering body temperature during forced hypothermia, the body uses various thermoregulatory effector mechanisms (i.e. shivering, non-shivering thermogenesis, peripheral vasoconstriction, and release of stress hormones) to generate heat and reduce heat loss (Frank et al. (1997) *Am J Physiol* 272:R557-R562). These thermoeffector responses are undesirable because the responses impede the efficacy of the cooling mechanism to reach the target temperature and are stressful and uncomfortable for the patient. Subjects undergoing forced hypothermia must be chemically sedated and paralyzed to reduce the stress on the patient from these thermoeffector responses. In addition, the stress of lowering body temperature from forced hypothermia transiently increases oxidative stress which may have an impact on ischemic organs (Katz et al. (2004) *Brain Res* 1017:85-91). In those patients with acute brain injuries, for example, hypothermia has a limited therapeutic window of opportunity and any delay and physiological stress that arises in reaching the target temperature will most likely have a negative impact on outcome (Clifton (2004) *Curr Opin Crit. Care* 10:116-119; Ginsberg (2003) *Stroke* 34:214-223; Kuboyama et al. (1993) *Crit. Care Med* 21:1348-1358). Therefore, other methods of inducing hypothermia for therapeutic purposes that result in a rapid induction of hypothermia with minimal stress on the patient are needed.

BRIEF SUMMARY OF THE INVENTION

Compositions and methods for inducing hypothermia in a subject are provided. The compositions find use in treating clinical insults, including but not limited to cerebral ischemic insults such as post cardiac arrest resuscitation neurological damage, stroke, or traumatic brain injury. The methods are also useful for maintaining regulated hypothermia in a subject for a prolonged period of time, and for reducing the time necessary to induce regulated hypothermia.

The compositions or multidrug combinations of the invention comprise a regulated hypothermic compound or a dopamine receptor agonist; a vasoactive compound; and an antiarrhythmic compound or a serotonin 5-$HT_3$ receptor antagonist. Additional agents can be included in the composition, including at least one of an antioxidant, a vitamin, N-acetylcysteine, and an antihyperglycemic compound. Various combinations of the drug components can be used. In some instances, the compositions of the invention comprise ethanol and optionally at least one of a vasoactive compound, an antihyperglycemic compound, a dopamine receptor agonist, an antiarrhythmic compound, a serotonin 5-$HT_3$ receptor antagonist, an antioxidant, a vitamin, and N-acetylcysteine. In those instances where the composition or multidrug combination comprises ethanol and optionally additional agents, the method of administration requires a two phase method of delivery of the composition as discussed below.

Presently disclosed methods include a method for inducing hypothermia in a subject comprising administering to the subject a multidrug combination comprising a regulated hypothermic compound or a dopamine receptor agonist; a vasoactive compound; and an antiarrhythmic compound or a serotonin 5-$HT_3$ receptor antagonist. It is recognized that the components of the multidrug combination may be administered together, separately, or in any combination thereof.

The invention further recognizes that a two phase delivery, a delivery of a high concentration of the multidrug combination followed by delivery of a lower concentration of the multidrug combination. This two phase method of delivery may be accomplished by a rapid infusion of the composition to induce hypothermia followed by a period of slow infusion, rapidly reducing the body temperature of a patient and maintaining the hypothermic state for a sustained period of time. Using this method of delivery, the composition may comprise a regulated hypothermic compound or a dopamine receptor agonist; a vasoactive compound; and an antiarrhythmic compound or a serotonin 5-HT$_3$ receptor antagonist and additional additives as discussed above. Additionally, using the two phase method of delivery, the composition may comprise ethanol and at least one of a vasoactive compound, an antiarrhythmic compound, a serotonin 5-HT$_3$ receptor antagonist, an antioxidant, a vitamin, N-acetylcysteine, and an antihyperglycemic compound. This two phase delivery method can be used to deliver any of the compositions of the invention and provides significant benefits to a patient.

In those embodiments wherein the clinical insult is of an acute nature, the methods are capable of preventing or limiting permanent injuries or stress, particularly if employed within the first few hours of the clinical insult. The methods find use in treating patients suffering from brain injuries, heart injuries, kidney injuries, cardiac bypass patients, patients suffering cardiac arrest, patients with neurologic injury, infants with hypoxic-ischemic encephalopathy, injuries of vital organs related to ischemia-reperfusion, patients who shiver, and the like. Thus, the methods can be used to reduce the stress and discomfort of shivering and to positively benefit and prevent injuries to the brain, heart, kidneys, and other organs. The methods lead to a reduction in mortality or a reduction in adverse effects attributed directly or indirectly to the clinical event.

The following embodiments are encompassed by the present invention:

1. A composition comprising:
   at least one regulated hypothermic compound or at least one dopamine receptor agonist;
   at least one vasoactive compound; and,
   at least one antiarrhythmic compound or at least one serotonin 5-HT$_3$ receptor antagonist.

2. The composition of embodiment 1, wherein said regulated hypothermic compound is selected from an aliphatic alcohol, neurotensin or an active analog thereof, or a thyroid compound.

3. The composition of embodiment 2, wherein said aliphatic alcohol is ethanol.

4. The composition of embodiment 2, wherein said thyroid compound is selected from the group consisting of propylthiouracil, thyroglobulin, thyrotropin-releasing hormone (TRH), and thyroid stimulating hormone (TSH).

5. The composition of embodiment 1, wherein said dopamine receptor agonist is a D$_2$ and D$_3$ receptor agonist.

6. The composition of embodiment 5, wherein said wherein said D$_2$ and D$_3$ receptor agonist is piribedil, bromocriptine, lusiride, or 7-OH-DPAT.

7. The composition of any one of embodiments 1-6, wherein said vasoactive compound is selected from dopamine, epinephrine, milirinone, or vasopressin.

8. The composition of embodiment 7, wherein said vasoactive compound is vasopressin.

9. The composition of any one of embodiments 1-8, wherein said antiarrhythmic compound is lidocaine or procainamide.

10. The composition of embodiment 9, wherein said antiarrhythmic compound is lidocaine.

11. The composition of any one of embodiments 1-8, wherein said serotonin 5-HT$_3$ receptor antagonist is tropisetron, granisetron, ondansetron, dolasetron, or palonosetron.

12. The composition of embodiment 11, wherein said serotonin 5-HT$_3$ receptor antagonist is ondansetron.

13. The composition of any one of embodiments 1-12, wherein said composition further comprises an antioxidant.

14. The composition of embodiment 13, wherein said antioxidant is selected from the list consisting of ascorbic acid, vitamin E, beta-carotene and a thiol-comprising compound.

15. The composition of embodiment 14, wherein said thiol-comprising compound is N-acetylcysteine.

16. The composition of any one of embodiments 1-15, wherein said composition further comprises a vitamin.

17. The composition of embodiment 16, wherein said vitamin is at least one of folate and thiamine.

18. The composition of any one of embodiments 1-17, wherein said composition further comprises an antihyperglycemic compound.

19. The composition of embodiment 18, wherein said antihyperglycemic compound is insulin or metformin.

20. The composition of embodiment 19, wherein said antihyperglycemic compound is insulin.

21. The composition of any one of embodiments 1-20, wherein said composition further comprises a pharmaceutically acceptable carrier.

22. A composition comprising ethanol, vasopressin, and lidocaine.

23. The composition of embodiment 22, wherein said composition further comprises at least one of an antioxidant, a vitamin, N-acetylcysteine, and an antihyperglycemic compound.

24. The composition of embodiment 22 or 23, wherein ethanol is present at a concentration of about 1 g/L to about 100 g/L; vasopressin is present at a concentration of about 1.0 U/L to about 4 U/L, and lidocaine is present at a concentration of about 20 mg/L to about 100 mg/L.

25. A method of treating a clinical insult in a subject, said method comprising administering to said subject a therapeutically effective amount of the composition of any one of embodiments 1-21 before, during, or following said clinical insult.

26. The method of embodiment 25, wherein said administering comprises administering the composition by rapid infusion followed by administering the composition by slow infusion.

27. The method of embodiment 26, wherein said rapid infusion comprises administration at an infusion rate of about 10 ml/kg/hr to about 80 ml/kg/hr.

28. The method of embodiment 27, wherein said rapid infusion comprises administration at an infusion rate of about 60 ml/kg/hr.

29. The method of any one of embodiments 26-28, wherein said slow infusion comprises administration at an infusion rate of about 1 ml/kg/hr to about 9 ml/kg/hr.

30. The method of embodiment 29, wherein said slow infusion comprises administration at an infusion rate of about 6 ml/kg/hr.

31. The method of any one of embodiments 25-30, wherein said clinical insult comprises an ischemic insult.

32. The method of embodiment 31, wherein said ischemic insult comprises a cerebral ischemic insult.

33. The method of embodiment 31, wherein said ischemic insult comprises a stroke, a cardiac arrest, asphyxia, a traumatic brain injury, a spinal cord injury, a near drowning, cardiac ischemia, tissue ischemia, or an invasive or vascular surgery.

34. The method of embodiment 33, wherein said cardiac arrest is an asphyxial cardiac arrest, a ventricular cardiac arrest, or a hemorrhagic cardiac arrest.

35. The method of embodiment 25, wherein said composition is administered to said subject within about 1 minute to about 72 hours following said ischemic insult.

36. The method of embodiment 35, wherein said composition is administered to said subject within about 1 minute to about 3 hours following said ischemic insult.

37. The method of any one of embodiments 26-34, wherein said rapid infusion of the composition is administered as soon as possible after said clinical insult.

38. The method of embodiment 37, wherein said rapid infusion of the composition is administered within about 5 minutes to about 3 hours following said clinical insult.

39. The method of any one of embodiments 37 or 38 wherein said slow infusion is administered within about 10 minutes to about 4 hours following said rapid infusion.

40. The method of embodiment 31 and 35-39, wherein said method further comprises transplanting at least one cell from said subject to an acceptor subject or acceptor site.

41. A method of treating an ischemic insult in a subject, said method comprising administering to said subject following said ischemic insult a therapeutically effective amount of ethanol wherein said administering comprises intravenous delivery of the ethanol by rapid infusion followed by intravenous delivery of the ethanol by slow infusion.

42. The method of embodiment 41, wherein said rapid infusion comprises administration at an infusion rate of about 10 ml/kg/hr to about 80 ml/kg/hr and said slow infusion comprises administration at an infusion rate of about 1 ml/kg/hr to about 9 ml/kg/hr.

43. The method of embodiment 42, wherein said rapid infusion comprises administration at an infusion rate of about 60 ml/kg/hr and said slow infusion comprises administration at an infusion rate of about 6 ml/kg/hr.

44. The method of any one of embodiments 41-44, wherein said therapeutically effective amount of ethanol comprises administering a composition having about a concentration of ethanol of about 5% to about 20%.

45. The method of any one of embodiments 41-44, wherein said rapid infusion of the composition is administered as soon as possible after said clinical insult.

46. The method of embodiment 45, wherein said rapid infusion of the composition is administered within about 5 minutes to about 3 hours following said chemical insult.

47. The method of any one of embodiments 45 or 46 wherein said slow infusion is administered within about 10 minutes to about 4 hours following said rapid infusion.

48. The method of any one of embodiments 41-47, wherein said method further comprises administering to said subject following said ischemic insult at least one of a vasoactive compound, an antiarrhythmic compound, an antioxidant, a vitamin, and an antihyperglycemic compound before, during, or following said ischemic insult.

49. A method of treating a clinical insult in a subject, said method comprising administering to said subject a therapeutically effective amount of a regulated hypothermic compound and a vasoactive compound before, during, or following said clinical insult wherein said administering comprises intravenous delivery of the regulated hypothermic compound and vasoactive compound by rapid infusion followed by intravenous delivery of the regulated hypothermic compound and vasoactive compound by slow infusion.

50. The method of embodiment 49, wherein said regulated hypothermic compound comprises an aliphatic alcohol, neurotensin or an active analog thereof, or a thyroid compound.

51. The method of embodiment 50, wherein said thyroid compound is selected from the group consisting of propylthiouracil, thyroglobulin, thyrotropin-releasing hormone (TRH), and thyroid stimulating hormone (TSH).

52. The method of embodiment 50, wherein said aliphatic alcohol comprises ethanol.

53. The method of embodiment 52, wherein between about 0.75 g/kg and about 10.0 g/kg of ethanol is administered to said subject.

54. The method of embodiment 53, wherein about 2.0 g/kg of ethanol is administered to said subject.

55. The method of any one of embodiments 49-54, wherein said vasoactive compound is selected from the list consisting of dopamine, epinephrine, milirinone, and vasopressin.

56. The method of embodiment 55, wherein said vasoactive compound comprises vasopressin.

57. The method of embodiment 56, wherein between about 0.005 U/kg and about 10 U/kg of vasopressin is administered to said subject.

58. The method of embodiment 57, wherein about 0.075 U/kg to about 2.0 U/kg of said vasopressin is administered to said subject.

59. The method of embodiment 58, wherein about 0.75 U/kg of said vasopressin is administered to said subject.

60. The method of any one of embodiments 49-59, wherein said method further comprises administering to said subject at least one of an antiarrhythmic compound, an antioxidant, a vitamin, and an antihyperglycemic compound before, during, or following said clinical insult.

61. The method of embodiment 60, wherein said antiarrhythmic compound comprises lidocaine or procainamide.

62. The method of embodiment 61, wherein said antiarrhythmic compound comprises lidocaine.

63. The method of embodiment 62, wherein between about 1 mg/kg and about 10 mg/kg of lidocaine is administered to said subject.

64. The method of embodiment 63, wherein about 2 mg/kg of lidocaine is administered to said subject.

65. The method of any one of embodiments 60-64, wherein said antioxidant is selected from the list consisting of ascorbic acid, vitamin E, beta-carotene, and a thiol-comprising compound.

66. The method of embodiment 65, wherein said thiol-comprising compound comprises N-acetylcysteine.

67. The method of embodiment 66, wherein between about 10 mg/kg and about 1200 mg/kg of N-acetylcysteine is administered to said subject.

68. The method of embodiment 67, wherein between about 50 mg/kg and about 300 mg/kg of N-acetylcysteine is administered to said subject.

69. The method of embodiment 68, wherein about 150 mg/kg N-acetylcysteine is administered to said subject.

70. The method of any one of embodiments 50-69, wherein said vitamin comprises at least one of folate and thiamine.

71. The method of embodiment 70, wherein between about 0.1 mg/kg and about 10 mg/kg of folate is administered to said subject.

72. The method of embodiment 71, wherein about 0.25 mg/kg folate is administered to said subject.

73. The method of embodiment 72, wherein between about 0.1 mg/kg and about 10 mg/kg of thiamine is administered to said subject.

74. The method of embodiment 73, wherein about 5 mg/kg of thiamine is administered to said subject.

75. The method of any one of embodiments 60-74, wherein said antihyperglycemic compound comprises metformin or insulin.

76. The method of embodiment 75, wherein said antihyperglycemic compound comprises insulin.

77. The method of embodiment 76, wherein between about 0.05 U/kg and about 10 U/kg of insulin is administered to said subject.

78. The method of embodiment 77, wherein about 0.25 U/kg insulin is administered to said subject.

BRIEF DESCRIPTION OF THE FIGURES

FIG. 1 shows the core temperature after cardiac arrest in swine receiving a rapid infusion for 40 minutes followed by a slow infusion. The multidrug combination included 63 g/L ethanol; 2.7 U/L vasopressin; and 66.7 mg/L lidocaine.

DETAILED DESCRIPTION OF THE INVENTION

The invention provides compositions and methods for inducing hypothermia in a subject. The methods find use in preventing or limiting permanent injuries to organs or tissues before, during, and following a clinical event. Regulated hypothermia is induced by providing a patient with a multidrug combination administered either as a single composition or as separate compositions. In some embodiments, the multidrug combinations comprise a regulated hypothermic compound or a dopamine receptor agonist; a vasoactive compound; and an antiarrhythmic compound or a serotonin 5-HT$_3$ receptor antagonist. Additional agents can be included in the composition including at least one of an antioxidant, a vitamin, N-acetylcysteine, and an antihyperglycemic compound. Various combinations of the drug components can be used. In other instances, the compositions of the invention comprise ethanol and, optionally, at least one of a vasoactive compound, an antihyperglycemic compound, a dopamine receptor agonist, an antiarrhythmic compound, a serotonin 5-HT$_3$ receptor antagonist, an antioxidant, a vitamin, and N-acetylcysteine. In those instances where the composition or multidrug combination comprises ethanol, and optionally additional agents, the method of administration requires a two phase method of delivery of the composition.

By "two phase method of delivery" is intended a delivery of a high concentration of the multidrug combination followed by delivery of a lower concentration of the multidrug combination. It is recognized that the concentration of multidrug combination delivered can be controlled by the concentration of the agents or compounds in the composition as well as by the rate of infusion of the composition into the patient. In one embodiment a composition comprising a high concentration of the multidrug combination will be administered, followed by a composition comprising a lower concentration of the agents of the multidrug combination. Alternatively, the two phase method of delivery may be achieved by administration of a single multidrug composition at a constant concentration delivered to a patient at a rapid infusion rate followed by administration of the same composition to the patient at a slower infusion rate.

The multidrug combinations and methods of the invention are useful in inducing regulated hypothermia in a patient and in improving survival in the patient suffering from hypoxia, ischemia, chemical toxicants, and other types of clinical insults to single or multiple organs. The methods involve the administration of a multidrug combination of the invention to reduce body temperature by the combination of lowering the brain's temperature set-point while maintaining the thermoregulation of the lower set point in the patient, decreasing metabolism, preventing shivering, and preventing peripheral vasoconstriction.

As used herein, the term "hypothermia" refers to a condition in a temperature-regulating organism (often referred to as a warm-blooded homeotherm) where the organism's core body temperature is below the normal core body temperature set point for the organism. In some embodiments, a hypothermic organism has a core body temperature that is at least about 1° C., about 2° C., about 3° C., about 4° C., about 5° C., about 6° C., about 7° C., about 8° C., about 9° C., about 10° C., or cooler than the normal core body temperature for the organism.

The term "core body temperature" reflects the internal temperature of an organism, as may be measured in the pulmonary artery, distal esophagus, nasopharynx, oral pharynx, bladder, rectum, or tympanic membrane. The surface body temperature can also be measured using thermal imaging techniques or skin temperature probes.

In some organisms, the normal core body temperature for an organism is about 37° C. and the hypothermic organism has a core body temperature of less than 37° C., including but not limited to, about 36° C., about 35.5° C., about 35° C., about 34.5° C., about 34° C., about 33.5° C., about 33° C., about 32.5° C., about 32° C., about 31.5° C., about 31° C., about 30.5° C., about 30° C., about 29.5° C., about 29° C., about 28.5° C., about 28° C., about 27.5° C., about 27° C., or cooler. In some embodiments of the invention, the presently disclosed compositions and multidrug combinations are administered to a patient to induce mild hypothermia, which refers to temperatures that are between about 2° C. and about 5° C. less than the normal core body temperature for an organism. Thus, in those organisms that have a normal core body temperature of about 37° C., mild hypothermia would be considered about 32° C. to less than about 35° C., including but not limited to about 32° C., about 32.5° C., about 33° C., about 33.5° C., about 34° C., about 34.5° C., and about 35° C.

The term "hypothermia" includes both forced hypothermia and regulated hypothermia. As used herein, "forced hypothermia" refers to hypothermia that is induced by lowering the core body temperature of an organism below the normal level dictated by the set-point temperature by overwhelming the body's capacity to thermoregulate. By "set-point temperature" is intended the value of core body temperature at which a healthy organism tends to stabilize by processes of thermoregulation such as heat gain, heat loss, and heat conservation. The "normal core body temperature" is the set-point temperature under normal physiological conditions.

Subjects undergoing forced hypothermia exhibit physiological and behavioral warming responses. Physiological warming responses are those responses of a subject to exposure to cold (i.e., temperatures below the normal core body temperature) or to stimuli that normally accompany cold in an effort to warm the subject. Physiological warming responses may include, but are not limited to, shivering, non-shivering thermogenesis, changes in blood flow (e.g., movement of blood away from the skin and extremities as a result of vasoconstriction, towards the body's core). Behavioral warming responses include movement of the subject towards warmer temperatures. Therefore, subjects undergoing forced hypothermia experience a decrease in core body temperature in spite of an increase in these heat-generating and conserving responses.

"Regulated hypothermia" refers to hypothermia that is induced via a reduction in the set-point temperature of an organism. Subjects undergoing regulated hypothermia exhibit physiological and behavioral cooling responses in an attempt to reduce the core body temperature to the lowered set-point temperature. Physiological cooling responses are those responses of a subject to warming, or to stimuli that usually accompany warming that serve to cool the animal.

Physiological cooling responses may include, but are not limited to, sweating, peripheral vasodilation, panting, drooling, licking, and decreases in metabolism. Behavioral cooling responses include movement of the subject towards cooler temperatures. Subjects undergoing regulated hypothermia undergo a decrease in core body temperature due to a decrease in activity of heat-generating/conserving responses and an increase in heat-dissipating responses.

While forced hypothermia using external and/or endovascular cooling methods reduces mortality and improves neurological outcome in some patients resuscitated from ventricular fibrillation or ventricular tachycardia cardiac arrest ((2002) N Engl J Med 346:549-556; Bernard et al. (2002) N Engl J Med 346:557-563; Tiainen (2007) Stroke 38:2303-2308), forced hypothermia is generally inefficient, slow, and ineffective for many injuries, including asphyxial cardiac arrest and cardiac arrests associated with pulseless electrical activity (PEA) (Kim et al. (2007) Circulation 115:3064-3070). The approximately three hours required to reach a target temperature of 33° C. with forced hypothermia is probably outside of the therapeutic window for hypoxic-ischemic brain injuries due to PEA cardiac arrest and asphyxial cardiac arrest (Arrich (2007) Crit. Care Med 35:1041-1047; Bernard (2004) Crit. Care Med 32:897-899; Clifton (2004) Curr Opin Crit. Care 10:116-119; Hoedemaekers et al. (2007) Crit. Care 11:R91; Jordan and Carhuapoma (2007) J Neurol Sci 261:35-38; Kim et al. (2007) Circulation 115:3064-3070).

Forced hypothermia methods are complicated because they require sedation with drugs such as benzodiazepams, analgesia with drugs such as narcotics and paralysis with drugs such as a smooth muscle depolarizing or non-depolarizing agents to "shut off" the normal thermoregulatory mechanisms that control cooling. The forced hypothermia methods in general are not portable, so delays often occur when initiating cooling and delays in cooling contribute to failure of forced hypothermia.

The regulated hypothermia of the present invention is a more efficient and rapid process for inducing hypothermia than forced hypothermic methods because the physiological responses of the subject undergoing regulated hypothermia facilitate a lowering of the body temperature, whereas subjects undergoing forced hypothermia exhibit physiological responses that combat a decrease in body temperature. The multidrug combination of the present invention can be administered anywhere in a hospital and anywhere outside of a hospital by emergency medical services (EMS), so there are likely to be fewer delays in initiating cooling. Therefore, regulated hypothermia is likely to be more effective in treating emergent insults that have a narrow therapeutic window compared with forced hypothermia. It is beneficial for the regulated hypothermia to be induced as soon as possible following a clinical insult. Thus, administration of the multidrug combination according to the methods of the invention should begin as soon as possible after the clinical insult.

Further, subjects undergoing regulated hypothermia are expected to undergo reduced discomfort in comparison to forced hypothermic methods. For example, regulated hypothermia can be performed on a conscious, spontaneously breathing subject because it avoids the need for sedating or paralyzing the patient to reduce shivering or other stresses associated with forced hypothermia. Thus, regulated hypothermia can be used on a wider range of patients than those currently eligible for therapeutic forced hypothermia. Regulated hypothermia has the added benefit of maintaining peripheral blood flow, contributing to a rapid rewarming during the recovery from hypothermic temperatures without the need for applied heat, which is often required for subjects recovering from forced hypothermia. The regulated hypothermia method is also likely to induce sweating which will aid in the rapidity of cooling since sweating is an efficient method of heat loss.

The presently disclosed subject matter provides for compositions and methods for treating a clinical insult in a subject comprising administering to the subject before, during, or following the insult a multidrug combination to induce regulated hypothermia. These multidrug combinations comprising regulated hypothermic compounds or dopamine receptor agonists can be used to protect all types of organelles, cells, tissues, and organs from damage due to ischemia or other types of clinical insults.

As indicated, in one embodiment the multidrug combinations comprise a regulated hypothermic compound or a dopamine receptor agonist; a vasoactive compound; and an antiarrhythmic compound or a serotonin 5-$HT_3$ receptor antagonist. Additional agents can be included selected from at least one of an antioxidant, a vitamin, N-acetylcysteine, and an antihyperglycemic compound. Other agents that may benefit the patient may also be included. By varying the components in the multidrug combination, one can design the combination for rapid cooling, prolonged duration of hypothermia, and the like. A reduction in the time needed to reach a hypothermic temperature or to lower the set-point temperature is especially important when hypothermia is needed to protect tissues from damage due to an acute insult such as ischemic insults, particularly tissues of highly aerobic organs, such as the brain, heart, and kidneys.

The multidrug combinations of the invention are administered to produce a rapid regulated hypothermic state in a patient. As discussed above, in one embodiment, the multidrug combination is administered in a two phase method of delivery. That is, a high concentration of the multidrug combination is delivered followed by delivery of a lower concentration of the multidrug combination. Thus, a composition comprising a high concentration of the multidrug combination may be delivered followed by administration of a composition comprising a lower concentration of the multidrug combination. Alternatively, the concentration of the multidrug combination is the same in the bolus or rapid infusion and in the subsequent slow infusion administration. However, when the concentration of the multidrug combination is the same in the composition, the rate of infusion will vary. That is, a single concentration of the multidrug combination can be used for both the bolus and the subsequent infusion. For the bolus a rapid infusion rate will be used. For the subsequent infusion, or slow infusion, administration of the multidrug combination will be at a slower infusion rate over time. The bolus, or rapid infusion, administered intravenously, allows a fast delivery which quickly raises the concentration of the multidrug combination in the blood to rapidly lower body temperature. The subsequent infusion, or slow infusion, at a slower rate maintains the lower body temperature in the patient. Thus, the bolus followed by a slow infusion rapidly produces the hypothermic state in a patient and prolongs the duration of hypothermia. The "rate of infusion" or "dosing rate" refers to the rate at which a drug is administered to achieve a steady state of a fixed dose which has been demonstrated to be therapeutically effective. In this manner, one of skill in the art can titrate the drug administration for the rapid and slow infusion rates to arrive at and maintain a desired body temperature.

Surprisingly the rapid administration of the multidrug combination does not raise blood glucose levels in the patient. It was expected that a rapid rate of administration of the multidrug combination would result in a rise in blood glucose levels in the patient, while a slower rate of administration would produce a lower rise in blood glucose levels. However, the opposite effect was observed. After the administration of the bolus (the rapid administration of the multidrug combination) following an acute ischemic insult, a reduction in blood glucose level is observed in the patient. Thus, the administration methods of the invention provide an additional benefit than merely rapidly reducing the body temperature of the patient.

It is recognized that the components of the multidrug combination may be admixed and administered together or provided separately. As noted above, the concentration of the components of the multidrug combination composition can be the same for the bolus and the subsequent infusion step. In this case, the invention has the additional advantage of being able to use a single syringe or single IV infusion set for administration of the bolus and the subsequent infusion. A sterile container (glass bottle, plastic bottle, or plastic bag) can be prefilled with the multidrug combination composition at a standard concentration and used for the bolus (rapid infusion) as well as the slow infusion. The flow rate of the IV infusion set can be adjusted to control flow or administration rate. Connectors can be used to allow "piggybacking" of another infusion set onto the same line to add a dose of another component. For example, where insulin is included in the multidrug combination it will be advantageous to keep the insulin separate from the ethanol prior to administration. In this manner, the insulin can be added by the addition of another infusion set onto the main line or syringe in the patient.

For controlling administration rates, an infusion pump can be used to control the flow rate and the total amount of multidrug combination delivered. A rapid infuser will be used for the administration of the bolus or the multidrug combination at a high flow rate.

Compositions and Multidrug Combinations

The presently disclosed subject matter provides compositions and multidrug combinations for inducing hypothermia, treating clinical insults, such as ischemic insults, and maintaining a regulated hypothermia for a prolonged period of time. In one embodiment, the multidrug combination comprises a regulated hypothermic compound or a dopamine receptor agonist; a vasoactive compound; and an antiarrhythmic compound or a serotonin 5-$HT_3$ receptor antagonist. Additional agents can be included in the composition including at least one of an antioxidant, a vitamin, N-acetylcysteine, and an antihyperglycemic compound. Various combinations of the drug components can be used. Typically, a regulated hypothermic compound or a dopamine receptor agonist; a vasoactive compound; and an antiarrhythmic compound or a serotonin 5-$HT_3$ receptor antagonist are included within the composition.

As used herein, a "regulated hypothermic compound" refers to a compound capable of inducing regulated hypothermia in a subject upon administration of an effective amount of the compound to the subject. The presently disclosed compositions may comprise any compound known in the art to induce regulated hypothermia, including but not limited to aliphatic alcohols, neurotensin and active analogs thereof, and thyroid compounds. As used herein, an "aliphatic alcohol" comprises an alcohol with a hydrocarbon group (comprising carbon and hydrogen), wherein the hydrocarbon can be linear, branched, or aromatic. Non-limiting examples of aliphatic alcohols include ethanol, methanol, isopropyl alcohol, n-butyl alcohol, t-butyl alcohol, isobutyl alcohol, isoamyl alcohol, n-hexyl alcohol, heptyl alcohol, n-octyl alcohol, n-nonyl alcohol, undecyl alcohol, and the like.

In some embodiments the regulated hypothermic compound can be substituted with a dopamine receptor agonist. While not bound to any theory of mechanism of action, it is not clear whether the dopamine receptor agonists of the invention are working as regulated hypothermic compounds. There may be some cooling effect with the individual use of these dopamine receptor agonists so they may be included with the definition of a regulated hypothermic compound. However, whatever the mode of action they are useful in the multidrug combinations of the invention. Accordingly for purposes of the invention the multidrug combination comprises a regulated hypothermic compound or a dopamine receptor agonist. Dopamine receptor agonists include $D_1$ receptor agonists, $D_2$ receptor agonists, $D_3$ receptor agonists, $D_4$ receptor agonists, $D_5$ receptor agonists, and $D_2$ and $D_3$ receptor agonists. In particular, $D_2$ and $D_3$ receptor agonists of interest include 2-[4-(benzo[1,3]dioxol-5-ylmethyl)piperazin-1-yl]pyrimidine (piribedil), Ergotaman-3',6',18-trione, 2-bromo-12'-hydroxy-2'-(1-methylethyl)-5' alpha-(2-methylpropyl)-(bromocriptine); 1,1-diethyl-3-((6aR,9S)-7-methyl-4,6,6a,7,8,9-hexahydroindolo[4,3-fg]quinolin-9-yl) urea (lusiride), 7-hydroxy-N,Ndipropyl-2-aminotetralin (7-OH-DPAT), and other dopamine agents that act as $D_2$ and $D_3$ receptor agonists and in some instances may have $\alpha 2$-adrenergic antagonist properties.

In some of those embodiments wherein the regulated hypothermic compound comprises ethanol, the concentration of ethanol (weight/volume) in the composition is between about 0.001 g/ml and about 0.15 g/ml, including but not limited to about 0.001 g·ml, about 0.005 g/ml, about 0.01 g/ml, about 0.03 g/ml, about 0.05 g/ml, about 0.06 g/ml, about 0.07 g/ml, about 0.08 g/ml, about 0.09 g/ml, about 0.10 g/ml, about 0.11 g/ml, about 0.12 g/ml, about 0.13 g/ml, about 0.14 g/ml, and about 0.15 g/ml. In certain embodiments, the concentration of ethanol in the composition is about 0.055 g/ml, about 0.057 g/ml, about 0.058 g/ml, about 0.06 g/ml, about 0.061 g/ml, about 0.062 g/ml, about 0.063 g/ml, about 0.064 g/ml, about 0.065 g/ml, about 0.67 about 0.068, about 0.11 g/ml, about 0.115 g/ml, about 0.12 g/ml, about 0.15 g/ml.

Neurotensin is a 13 amino acid neuropeptide, the amino acid sequence of which is set forth in SEQ ID NO: 1, that regulates the release of leutenizing hormone and prolactin. An analog of neurotensin refers to a polypeptide analog of neurotensin, which may have an amino acid sequence that is longer, shorter, or the same length as the amino acid sequence of neurotensin. Neurotensin analogs may include non-naturally-occurring amino acids and may also include non-amino acid compounds. An active analog of neurotensin is an analog that can effectively induce regulated hypothermia upon administration to a subject, and can include but is not limited to the neurotensin analogs NT64D, NT64L, NT65L, NT66D, NT66L, NT67L, NT69L, NT69L, NT71, NT72, NT73, NT74, NT75, NT76, and NT77, and neurotensin analogs comprising neo-tryptophan as described in U.S. Pat. No. 7,319,090, which is herein incorporated by reference in its entirety. The amino acid sequences and methods of making these neurotensin analogs are described in U.S. Pat. No. 6,214,790, which is hereby incorporated by reference in its entirety.

"Thyroid compounds" refer to compounds that lead to a state of hypothyroidism, a condition characterized by lower than normal levels of thyroid hormones (thyroxine, T4, and triiodothyronine, T3). Hypothyroidism, which can be induced through the administration of compounds such as propylthiouracil (PTU), has been shown to induce a state of regulated hypothermia (Yang and Gordon (1997) *American Journal of Physiology* 41:R1390-R1395, which is herein incorporated by reference in its entirety). Non-limiting examples of thyroid compounds that can be used in the presently disclosed compositions and methods include propylthiouracil, thyroglobulin, thyrotropin-releasing hormone (TRH), and thyroid stimulating hormone (TSH).

As used herein, a "vasoactive compound" refers to a compound capable of dilating or constricting blood vessels upon administration to a subject. Vasoactive compounds encompass both vasodilatory and vasoconstrictive compounds. In some embodiments, the vasoactive compound comprises a vasoactive compound capable of both vasodilation in combination with peripheral vasoconstriction. A non-limiting example of such a compound is vasopressin, which is also referred to as argipressin or antidiuretic hormone. In other embodiments, the vasoactive compound comprises a vasoconstrictive compound. Vasoconstrictive compounds generally increase peripheral vascular resistance and increase blood pressure. In some embodiments, the vasoactive compound can increase cardiac contractility and reduce afterload, thus increasing blood flow. Non-limiting examples of vasoactive compounds suitable for use in the presently disclosed compositions and methods include phenylephrine, pseudoephedrine, dopamine, norepinephrine, epinephrine, milirinone, and vasopressin. "Vasopressin" refers to a nonapeptide hormone, the sequence of which is set forth in SEQ ID NO: 2. A vasopressin precursor or an active analog of vasopressin may also be used in the presently disclosed compositions or methods. An analog of vasopressin refers to a polypeptide analog of vasopressin, which may have an amino acid sequence that is longer, shorter, or the same length as the amino acid sequence of vasopressin. Vasopressin analogs may include non-naturally-occurring amino acids and may also include non-amino acid compounds. An active analog of vasopressin is an analog that retains the activity of the parent vasopressin compound (e.g., its vasoactive effects).

In certain embodiments wherein the composition or multidrug combination comprises a regulated hypothermic compound and a vasoactive compound, the vasoactive compound comprises vasopressin, and in other embodiments, the regulated hypothermic compound comprises ethanol. In still other embodiments, the composition or multidrug combination comprises vasopressin and ethanol.

In some of those embodiments wherein the vasoactive compound comprises vasopressin, the concentration of vasopressin (weight/volume) in the composition is about 0.00001 U/ml, about 0.0001 U/ml, about 0.001 U/ml, about 0.002 U/ml, about 0.0025 U/ml, about 0.0027 U/ml, about 0.0028 U/ml, about 0.003 U/ml, about 0.0035 U/ml, about 0.004 U/ml, about 0.0045 U/ml, about 0.005 U/ml, about 0.006 U/ml, about 0.007 U/ml, about 0.008 U/ml, about 0.009 U/ml, about 0.01 U/ml, about 0.02 U/ml, about 0.03 U/ml, about 0.04 U/ml, about 0.05 U/ml, about 0.06 U/ml, about 0.07 U/ml, about 0.08 U/ml, about 0.09 U/ml, up to about 0.1 U/ml.

While not being bound by any theory or mechanism of action, it is believed the vasoactive compound serves to enhance the circulation of the other components of the composition, contributing to a more rapid induction of hypothermia. In addition, the vasoactive drug unexpectedly reduces time to reach hypothermia and prolongs the duration of hypothermia. A reduction in the time needed to reach a hypothermic temperature is especially useful for the treatment of acute insults, such as ischemia, where early intervention is key to improving patient outcome. The duration of hypothermia may also be important, with longer durations of hypothermia potentially needed for more severe insults and the vasoactive compound serves to enhance the duration of the hypothermia.

As indicated, the multidrug combination comprises an antiarrhythmic compound or a serotonin 5-$HT_3$ receptor antagonist. As used herein, an "antiarrhythmic compound" refers to compounds that are capable of suppressing abnormal rhythms of the heart (cardiac arrhythmias), which can include abnormally fast rhythms including but not limited to atrial fibrillation, atrial flutter, ventricular tachycardia, and ventricular fibrillation, and abnormally slow rhythms. Antiarrhythmic compounds have been classified into five main classes based on their primary mechanism of action (see Vaughan Williams (1970) "Classification of anti-arrhythmic drugs." In: *Symposium on Cardiac Arrhythmias*, Sandfte E, Flensted-Jensen E, Olesen K H eds. Sweden, AB ASTRA, Södertälje, 449-472, which is herein incorporated by reference in its entirety). Non-limiting examples of antiarrhythmic compounds include class IA compounds such as quinidine, procainamide, and disopyramide; class IB compounds such as lidocaine, phenyloin, and mexiletine; class Ic compounds such as flecainide, propafenone, and moricizine; class II compounds such as propranolol, esmolol, timolol, metoprolol, and atenolol; class III compounds such as amiodarone, sotalol, ibutilide, and dofetilide; class IV compounds such as verapamil and diltiazem; and class V compounds such as adenosine and digoxin. Additional antiarrhythmic compounds suitable for use in the presently disclosed methods and compositions can be found in Opie (1997) Drugs for the Heart; W.B. Saunders Company, which is herein incorporated by reference in its entirety. In some embodiments, the antiarrhythmic compound is procainamide or lidocaine.

In some of those embodiments wherein the antiarrhythmic compound comprises lidocaine (2-(diethylamino)-N-(2,6-dimethylphenyl)acetamide), the concentration of lidocaine in the composition (weight/volume) is between about 0.05 mg/ml and about 0.25 mg/ml, including but not limited to about 0.05 mg/ml, about 0.055 mg/ml, about 0.057 mg/ml, about 0.06 mg/ml, about 0.062 mg/ml, about 0.064 mg/ml, about 0.065 mg/ml, about 0.066 mg/ml, about 0.067 mg/ml, about 0.068 mg/ml, about 0.069 mg/ml, about 0.07 mg/ml, about 0.073 mg/ml, about 0.075 mg/ml, about 0.078 mg/ml, about 0.08 mg/ml, about 0.09 mg/ml, about 0.10 mg/ml, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.20 mg/ml, about 0.21 mg/ml, about 0.22 mg/ml, about 0.23 mg/ml, about 0.24 mg/ml, and about 0.25 mg/ml. In certain embodiments, the concentration of lidocaine in the composition is about 0.062 mg/ml, about 0.064 mg/ml, about 0.065 mg/ml, about 0.066 mg/ml, about 0.067 mg/ml, about 0.068 mg/ml, about 0.069 mg/ml, about 0.07 mg/ml, about 0.11 mg/ml.

A serotonin 5-$HT_3$ receptor antagonist may also be included in the multidrug combination. 5-$HT_3$ receptor antagonists are a class of medications that act as receptor antagonists at the 5-hydroxytryptamine-3 receptor (5-$HT_3$ receptor). 5-$HT_3$ receptor antagonists have been used in the prevention and treatment of chemotherapy-induced nausea and vomiting. 5-$HT_3$ receptor antagonists of interest include, but are not limited to, (RS)-9-methyl-3-[(2-methyl-1H-imidazol-1-yl)methyl]-2,3-dihydro-1H-carbazol-4(9M-one (ondansetron), (1R,5S)-8-methyl-8-azabicyclo[3.2.1]octan-3-yl 1methyl-indole-3-carboxylate (tropisetron), 1-methyl-N-((1R,3r,5S)-9-methyl-9-azabicyclo[3.3.1]nonan-3-yl)-1H-indazole-3-carboxamide (granisetron), (3R)-10-oxo-8-azatricyclo[5.3.1.0$^{3,8}$]undec-5-yl 1H-indole-3-carboxylate (dolasetron), (3aR)-2-[(3S)-1-azabicyclo[2.2.2]oct-3-yl]-2,3,3a,4,5,6-hexahydro-1H-benz[de]isoquinolin-1-one (palonosetron), (1-methyl-1H-indol-3-yl)[(5R)-4,5,6,7-tetrahydro-1H-benzimidazol-5-yl]methanone (ramosetron) and the like.

In addition to the regulated hypothermic compound or dopamine receptor agonist; vasoactive compound; and anti-arrhythmic compound or serotonin 5-HT$_3$ receptor antagonist, additional agents can be included in the composition. Such additional agents include at least one of an antioxidant, a vitamin, N-acetylcysteine, and an antihyperglycemic compound.

In some embodiments the composition or multidrug combination can comprise ethanol, vasopressin, and lidocaine. In some of these embodiments, the concentration of ethanol in the composition is between about 0.05 g/ml and about 0.15 g/ml, the concentration of vasopressin is between about 0.001 U/ml and about 0.1 U/ml, the concentration of lidocaine is between about 0.05 mg/ml and about 0.25 mg/ml. In other embodiments, the composition comprises about 0.11 g/ml (about 2.4 M) ethanol, about 0.011 U/ml vasopressin, about 0.11 mg/ml (about $4.74 \times 10^{-4}$ M) lidocaine, and about 5.1 mg/ml (about $3.125 \times 10^{-2}$ M) N-acetylcysteine. In these embodiments, the molar ratio of ethanol:N-acetylcysteine:lidocaine is about 5063:66:1. Thus, in some embodiments, the composition comprises a molar ratio of ethanol:N-acetylcysteine:lidocaine of about 5063:66:1.

The compositions and multidrug combinations of the invention can comprise a vitamin. As used herein, the term "vitamin" refers to an organic compound that is essential in relatively small quantities to the normal metabolism of a living organism. Non-limiting examples of vitamins include vitamin A (retinol), vitamin B$_1$ (thiamine), vitamin C (ascorbic acid), vitamin D (calciferol), vitamin B$_2$ (riboflavin), vitamin E (tocopherol), vitamin B$_{12}$ (cyanocobalamin), vitamin K (phylloquinone), vitamin B$_5$ (pantothenic acid), vitamin B$_7$ (biotin), vitamin B$_6$ (pyridoxine), vitamin B$_3$ (niacin), and vitamin B$_9$ (folic acid).

In some embodiments, particularly those embodiments wherein the regulated hypothermic compound of the composition comprises ethanol, the composition comprises a B complex vitamin. Non-limiting examples of B complex vitamins useful for the presently disclosed methods include folate or folic acid and thiamine. Without being bound by any theory or mechanism of action, it is believed that prophylactic replacement of the two most common vitamins potentially depleted by ethanol, thiamine and folate, will prevent delays in recovery of enzymatic activities enabled with these vitamins.

In other embodiments, the composition or multidrug combination comprises an antioxidant. As used herein, an "antioxidant" refers to a molecule capable of slowing or preventing the oxidation of other molecules. Non-limiting examples of antioxidants include dihydropyridines, polyphenols, flavonoids, isoprenoids, retinoids, inhibitors of mitochondrial function, inhibitors of glycolysis, inhibitors of glycogen synthase kinase, inhibitors of flavoprotein oxidases, iron/zinc chelators, inhibitors of lipoxygenases, inhibitors of protein kinase C, inhibitors of PI3-kinase, inhibitors of tyrosine kinases, and estrogen agonists. In some embodiments, the antioxidant can be selected from the group consisting of vitamin E, beta-carotene, ascorbic acid, and a thiol-comprising compound (i.e., compounds comprising the functional group composed of a sulfur and a hydrogen atom, referred to as —SH), such as glutathione and the glutathione precursor N-acetylcysteine. In particular embodiments, the antioxidant comprises N-acetylcysteine ((2R)-2-acetamido-3-sulfanylpropanoic acid). Where the antioxidant comprises N-acetylcysteine, the concentration of N-acetylcysteine in the composition (weight/volume) is between about 0.5 mg/ml and about 50 mg/ml, including but not limited to about 0.5 mg/ml, about 1 mg/ml, about 5 mg/ml, about 10 mg/ml, about 20 mg/ml, about 30 mg/ml, about 40 mg/ml, and about 50 mg/ml. In certain embodiments, the concentration of N-acetylcysteine in the composition is about 5.1 mg/ml.

In one embodiment, the composition or multidrug combination can comprise a regulated hypothermic compound, a vasoactive compound, an antiarrhythmic compound, an antioxidant, and a vitamin. In some of these embodiments, the regulated hypothermic compound comprises ethanol, in other embodiments, the vasoactive compound comprises vasopressin, in still other embodiments, the antiarrhythmic compound comprises lidocaine, in yet other embodiments, the antioxidant comprises N-acetylcysteine, and in certain embodiments, the vitamin comprises folate and thiamine. In particular embodiments, the composition or multidrug combination comprises ethanol, vasopressin, lidocaine, N-acetylcysteine, folate, and thiamine.

In other embodiments an antihyperglycemic compound can be included in the multidrug combination. As used herein, the term "antihyperglycemic compound" refers to a compound capable of reducing the blood glucose level (which can be normal or elevated) upon administration to a subject. Non-limiting examples of antihyperglycemic compounds include insulin, sulfonylureas (such as tolbutamide, acetohexamide, tolazamide, chlorpropamide, glipizide, glyburide, glimepiride, and gliclazide); meglitinides (such as repaglinide and nateglinide); biguanides (such as metformin, phenformin, and buformin); thiazolidinediones (such as rosiglitazone, pioglitazone, and troglitazone); alpha-glucosidase inhibitors (such as miglitol and acarbose); incretin mimetics (such as exenatide, liraglutide, and taspoglatide); dipeptidyl peptidase-4 inhibitors (such as vildagliptin and sitagliptin); and amylin analogues.

In some of the embodiments wherein the composition or multidrug combination comprises a regulated hypothermic compound and an antihyperglycemic compound, the regulated hypothermic compound comprises ethanol, and in other embodiments, the antihyperglycemic compound comprises insulin. In particular embodiments, the composition or multidrug combination comprises ethanol and insulin. In other embodiments, the composition or multidrug combination comprises: ethanol, vasopressin, and insulin; ethanol, N-acetylcysteine, and insulin; ethanol, lidocaine, and insulin; ethanol, folate, thiamine, and insulin; ethanol, vasopressin, N-acetylcysteine, and insulin; ethanol, vasopressin, lidocaine, and insulin; ethanol, vasopressin, folate, thiamine, and insulin; ethanol, lidocaine, folate, thiamine, and insulin; ethanol, lidocaine, N-acetylcysteine, and insulin; ethanol, folate, thiamine, N-acetylcysteine, and insulin; ethanol, vasopressin, lidocaine, folate, thiamine, and insulin; ethanol, vasopressin, lidocaine, N-acetylcysteine, and insulin; ethanol, vasopressin, N-acetylcysteine, folate, thiamine, and insulin; ethanol, lidocaine, N-acetylcysteine, thiamine, folate, and insulin; and ethanol, vasopressin, lidocaine, N-acetylcysteine, folate, thiamine, and insulin.

The presently disclosed compositions or components of the multidrug combinations can be formulated for delivery, i.e., administering to the subject, by any available route including, but not limited, to parenteral (e.g., intravenous), intradermal, subcutaneous, oral, nasal, bronchial, opthalmic, transdermal (topical), transmucosal, etc. Generally, the route of delivery is intravenous.

The presently disclosed compositions or components of the multidrug combinations can additionally include a pharmaceutically acceptable carrier. As used herein the term "pharmaceutically acceptable carrier" includes solvents, dispersion media, coatings, antibacterial and antifungal agents, isotonic, hypertonic saline, absorption delaying agents, agents to slow the degradation of a protein by an alcohol, and the like, compatible with pharmaceutical administration. Supplementary active compounds also can be incorporated into the formulations.

As one of ordinary skill in the art would appreciate, a presently disclosed pharmaceutical formulation is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. pH can be adjusted with acids or bases, such as hydrochloric acid, sodium bicarbonate, or sodium hydroxide. The parenteral preparation can be enclosed in ampules, disposable syringes or multiple dose vials made of glass or plastic.

Pharmaceutical formulations suitable for injectable use typically include sterile aqueous solutions (where water soluble) or dispersions and sterile powders for the extemporaneous preparation of sterile injectable solutions or dispersions. For intravenous administration, suitable carriers include physiological saline, hypertonic saline, bacteriostatic water, Cremophor EL™ (BASF, Parsippany, N.J.) or phosphate buffered saline (PBS). The composition should be sterile and should be fluid to the extent that easy syringability exists. Preferred pharmaceutical formulations are stable under the conditions of manufacture and storage and should be preserved against the contaminating action of microorganisms, such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. In some of those embodiments wherein the composition comprises ethanol as the regulated hypothermic compound, ethanol can serve as the carrier for the additional compounds of the composition. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols, such as manitol or sorbitol, or sodium chloride in the formulation. In some embodiments, hypertonic agents can be included in the formulation. Prolonged absorption of the injectable formulation can be brought about by including in the formulation an agent that delays absorption, for example, aluminum monostearate and gelatin.

Sterile injectable solutions can be prepared by incorporating the active compound(s) in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above.

Oral formulations generally include an inert diluent or an edible carrier. Alternatively, in those embodiments wherein ethanol is the regulated hypothermic compound, ethanol can serve as the diluent for the other compounds of the composition. For the purpose of oral therapeutic administration, the active compound(s) can be incorporated with excipients and used in the form of tablets, troches, or capsules, e.g., gelatin capsules. Formulations for oral delivery can advantageously incorporate agents to improve stability within the gastrointestinal tract and/or to enhance absorption.

For administration by inhalation, the presently disclosed formulations are preferably delivered in the form of an aerosol spray from a pressurized container or dispenser which contains a suitable propellant, e.g., a gas such as carbon dioxide, or a nebulizer. Liquid aerosols, dry powders, and the like, also can be used.

Systemic administration of the presently disclosed formulations also can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The presently disclosed formulations also can be prepared with carriers that will protect the compound(s) against rapid elimination from the body, such as a controlled release formulation, including implants, microencapsulated delivery systems, and nanoparticles. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials also can be obtained commercially from Alza Corporation and Nova Pharmaceuticals, Inc. Liposomal suspensions (including liposomes targeted to infected cells with monoclonal antibodies to viral antigens) also can be used as pharmaceutically acceptable carriers. Such suspensions can be prepared according to methods known to those skilled in the art, for example, as described in U.S. Pat. No. 4,522,811, which is incorporated herein by reference in its entirety.

In some embodiments, at least one of the compounds of the presently disclosed compositions can be stored as a separate component and each of the compounds can be mixed (optionally with a pharmaceutically acceptable carrier) immediately prior to administration to the subject. This practice can minimize interactions between the compounds of the composition that in some instances can lead to inactivation or a reduction in the effectiveness of the compounds. For example, when ethanol and insulin are included within the multidrug combination, it will be advantageous to store the components separately. At the time of administration, the components will be mixed or will be administered together. In one embodiment, the components of the multidrug combination can be provided in a kit wherein they can be stored in separate containers or in a single container except when an antihyperglycemic compound is provided as a component of the combination. When an antihyperglycemic compound will be administered, it will be stored separately from the regulated hypothermic compound, particularly when the regulated hypothermic compound is ethanol.

When the components of the multidrug combination are provided separately, they can still be administered with a single infusion syringe or single IV infusion set as discussed above. The container or containers can be prefilled with a single or multiple components of the multidrug combination and administered. Connectors can be used in the IV infusion line to allow additional infusion lines onto the infusion syringe or IV infusion set.

Thus, a therapeutically effective amount of each of the components of a particular multidrug combination described herein may be administered separately, for example, as individual compositions, or as a single composition, for example, a composition disclosed herein. Where the components are administered separately, the individual components can be administered in any order, concurrently or separately. That is, administration of the drug components of interest can be simultaneous (concurrent), consecutive (sequential), or a combination thereof. Therefore, a subject undergoing treatment with a multi-drug combination described herein can receive all of the drug components at the same time (i.e., simultaneously or concurrently) or at different times (i.e., sequentially, in any order), so long as the desired therapeutic effect of the multi-drug combination is caused in the subject undergoing therapy. In some embodiments, the multi-drug combination is given simultaneously for one dosing, but other dosings include sequential administration of the drug components, in any order. Where the drug components are administered simultaneously, they can be administered as separate pharmaceutical compositions or can be administered as a single pharmaceutical composition comprising all of the drug components.

Methods

The presently disclosed subject matter provides methods of inducing and/or maintaining hypothermia in a subject in need thereof. Methods of inducing hypothermia in a subject comprise administering to the subject a therapeutically effective amount of a multidrug combination or composition of the invention. It is beneficial in the practice of the invention to begin therapy by a rapid infusion (or bolus administration) of the multidrug combination to quickly lower the body temperature of the patient followed by a subsequent or slow infusion of the multidrug combination to maintain the hypothermic state of the patient.

By "rapid infusion" or "bolus" is intended that a therapeutically effective amount of the multidrug combination is administered at a rate of about 10 ml/kg/hr, about 15 ml/kg/hr, about 20 ml/kg/hr, about 30 ml/kg/hr, about 40 ml/kg/hr, about 50 ml/kg/hr, about 55 ml/kg/hr, about 60 ml/kg/hr, about 65 ml/kg/hr, about 70 ml/kg/hr, about 80 ml/kg/hr, about 90 ml/kg/hr, about 100 ml/kg/hr, about 110 ml/kg/hr, to about 120 ml/kg/hr.

By "slower infusion" or "subsequent infusion" is intended that a therapeutically effective amount of the multidrug combination is administered at a rate of about 1 ml/kg/hr, about 1.5 ml/kg/hr, about 2 ml/kg/hr, about 2.5 ml/kg/hr, about 3 ml/kg/hr, about 3.5 ml/kg/hr, about 4 ml/kg/hr, about 5 ml/kg/hr, about 6 ml/kg/hr, about 7 ml/kg/hr, about 8 ml/kg/hr, up to about 9 ml/kg/hr.

These rates of infusion are based on the delivery of a therapeutically effective amount of the multidrug combination to the patient. As discussed, the same composition or combination of compositions of the multidrug combination can be used for both the rapid and the slow infusion. The rate of infusion will provide a therapeutic amount for either the rapid infusion or the slow infusion. In general, concentrations of components that may be included in the multidrug combination and provide a therapeutically effective amount include:

ethanol (about 1%, about 2%, about 3%, about 4%, about 5%, about 6%, about 7%, about 8%, about 9%, about 10%, about 11%, up to about 20%; or about 0.5 g/kg, about 1 g/kg, about 1.5 g/kg, about 2.0 g/kg, about 2.5 g/kg, about 3.0 g/kg, about 3.5 g/kg, about 4 g/kg, about 5 g/kg, about 6 g/kg, about 7 g/kg, about 8 g/kg, about 9 g/kg, up to about 10 g/kg; or about 1 g/L, about 2 g/L, about 3 g/L, about 4 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, about 100 g/L, about 110 g/L, about 120 g/L, about 130 g/L, about 140 g/L, up to about 150 g/L);

vasopressin (about 0.01 U/L, about 0.03 U/L, about 0.05 U/L, about 0.07 U/L, about 0.1 U/L, about 0.3 U/L, about 0.5 U/L, about 0.7 U/L, about 1.0 U/L, about 1.5 U/L, about 2.0 U/L, about 2.2 U/L, about 2.4 U/L, about 2.5 U/L, about 2.6 U/L, about 2.7 U/L, about 2.8 U/L, about 2.9 U/L, about 3.0 U/L, about 3.2 U/L, about 3.4 U/L, about 3.6 U/L, about 3.8 U/L, about 4.0 U/L, about 4.2 U/L, about 4.4 U/L, about 4.7 U/L, about 5.0 U/L, about 5.3 U/L, about 5.5 U/L, about 5.7 U/L, about 6.0 U/L, about 6.3 U/L, about 6.5 U/L, about 6.7 U/L, about 7.0 U/L, about 10 U/L, about 15 U/L, about 20 U/L, about 25 U/L, about 30 U/L, about 40 U/L, about 50 U/L, about 60 U/L, about 70 U/L, about 80 U/L, up to about 100 U/L);

lidocaine (about 40 mg/L; about 45 mg/L; about 50 mg/L; about 55 mg/L; about 57 mg/L; about 58 mg/L; about 59 mg/L; about 60 mg/L; about 61 mg/L; about 62 mg/L; about 63 mg/L; about 64 mg/L; about 65 mg/L; about 66 mg/L; about 67 mg/L; about 68 mg/L; about 69 mg/L; about 70 mg/L; about 72 mg/L; about 75 mg/L; about 77 mg/L; about 80 mg/L; up to about 85 mg/L);

odansetron (about 1 mg/L, about 1.5 mg/L, about 2 mg/L; about 2.5 mg/L; about 2.8 mg/L; about 3.0 mg/L; about 3.3 mg/L; about 3.5 mg/L; about 3.7 mg/L; about 4.0 mg/L; about 4.1 mg/L; about 4.2 mg/L; about 4.3 mg/L; about 4.4 mg/L; about 4.5 mg/L; about 4.6 mg/L; about 4.7 mg/L; about 4.8 mg/L; about 4.9 mg/L; about 5.0 mg/L; about 5.2 mg/L; about 5.4 mg/L; about 5.6 mg/L; about 5.8 mg/L; up to about 6.0 mg/L);

7-OH-DPAT (about 7 mg/l, about 7.5 mg/L, about 8.0 mg/L, about 8.3 mg/L, about 8.5 mg/L, about 8.8 mg/L, about 9.0 mg/L, about 9.3 mg/L, about 9.5 mg/L, about 9.7 mg/L, about 10 mg/L, about 10.3 mg/L, about 10.5 mg/L, about 10.7 mg/L, about 11 mg/L, about 11.3 mg/L, about 11.5 mg/L, about 11.7 mg/L, about 12 mg/L, about 12.3 mg/L, about 12.5 mg/L, about 12.7 mg/L, about 13 mg/L, about 13.3 mg/L, about 13.5 mg/L, about 13.7 mg/L, about 14 mg/L, about 14.3 mg/L, about 14.5 mg/L, about 14.7 mg/L, about 15 mg/L, about 15.3 mg/L, about 15.5 mg/L, about 15.7 mg/L, about 16 mg/L, about 16.1 mg/L, about 16.2 mg/L, about 16.3 mg/L, about 16.4 mg/L, about 16.5 mg/L, about 16.6 mg/L, about 16.7 mg/L, about 16.8 mg/L, about 16.9 mg/L, about 17 mg/L, about 17.1 mg/L, about 17.2 mg/L, about 17.3 mg/L, about 17.5 mg/L, about 17.7 mg/L, about 18 mg/L, about 18.5 mg/L, about 19 mg/L, about 19.5 mg/L, about 20 mg/L, about 20.5 mg/l, up to about 21 mg/L).

When the following compounds or agents are included in the composition, the bolus dose or rapid infusion dose for the components of the multidrug combination is: ethanol (about 1 g/kg, about 1.5 g/kg, about 2.0 g/kg, about 2.5 g/kg, about 3.0 g/kg, about 3.5 g/kg, about 4 g/kg, about 4.5 g/kg, about 5.0 g/kg, about 5.5 g/kg, about 6.0 g/kg, about 6.5 g/kg, about 7.0 g/kg, about 8 g/kg, about 9 g/kg, about 10 g/kg, about 11 g/kg, about 12 g/kg, about 13 g/kg, about 14 g/kg, up to about 20 g/kg);

vasopressin (about 0.001 U/kg, about 0.005 U/kg, about 0.007 U/kg, about 0.01 U/kg, about 0.015 U/kg, about 0.017 U/kg, about 0.02 U/kg, about 0.025 U/kg, about 0.03 U/kg, about 0.035 U/kg, about 0.04 U/kg, about 0.045 U/kg, about 0.05 U/kg, about 0.055 U/kg, about 0.06 U/kg, about 0.065 U/kg, about 0.07 U/kg, about 0.075 U/kg, about 0.08 U/kg, about 0.085 U/kg, about 0.09 U/kg, about 0.095 U/kg, up to about 0.1 U/kg, about 0.5 U/kg, about 1.0 U/kg/about 1.5 U/kg, about 2.0 U/kg, about 2.5 U/kg, about 3.0 U/kg, about 3.5 U/kg, about 4.0 U/kg, about 4.5 U/kg, about 5.0 U/kg, about 5.5 U/kg, about 6.0 U/kg, about 6.5 U/kg, about 7.0 U/kg, about 7.5 U/kg, about 8.0 U/kg, about 8.5 U/kg, about 9.0 U/kg, about 9.5 U/kg, about 10.0 U/kg, about 11 U/kg, about 12 U/kg, about 13 U/kg, about 14 U/kg, about 15 U/kg, about 20 U/kg, about 25 U/kg, about 30 U/kg, about 40 U/kg, up to about 50 U/kg);

lidocaine (about 1 mg/kg, about 1.3 mg/kg, about 1.5 mg/kg, about 1.7 mg/kg, about 2.0 mg/kg, about 2.3 mg/kg, about 2.5 mg/kg, about 3.0 mg/kg, about 3.3 mg/kg, about 3.5 mg/kg, about 3.7 mg/kg, about 4.0 mg/kg, about 4.3 mg/kg, about 4.5 mg/kg, about 4.8 mg/kg, about 5.0 mg/kg, about 5.5 mg/kg, about 6.0 mg/kg, about 6.5 mg/kg, about 7.0 mg/kg, about 7.5 mg/kg, about 8.0 mg/kg, about 8.5 mg/kg, about 9.0 mg/kg, about 10 mg/kg, about 11 mg/kg, about 12 mg/kg, about 15 mg/kg, about 18 mg/kg, up to about 20 mg/kg);

odansetron (about 0.01 mg/kg, about 0.03 mg/kg, about 0.05 mg/kg, about 0.07 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, up to about 5.0 mg/kg);

7-OH-PDAT (0.01 mg/kg, about 0.05 mg/kg, about 0.1 mg/kg, about 0.15 mg/kg, about 0.2 mg/kg, about 0.25 mg/kg, about 0.3 mg/kg, about 0.35 mg/kg, about 0.40 mg/kg, about 0.45 mg/kg, about 0.5 mg/kg, about 0.6 mg/kg, about 0.7 mg/kg, about 0.8 mg/kg, about 1.0 mg/kg, about 1.5 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 8.5 mg/kg, about 9.0 mg/kg, about 9.5 mg/kg, about 10.0 mg/kg, about 12 mg/kg, about 15 mg/kg, about 18 mg/kg, about 20 mg/kg, about 25 mg/kg, about 30 mg/kg, about 35 mg/kg, about 40 mg/kg, about 45 mg/kg, up to about 50 mg/kg);

bromocriptine (about 0.01 mg/kg, about 0.05 mg/kg, about 0.1 mg/kg, about 0.5 mg/kg, about 1.0 mg/kg, about 5 mg/kg, about 10 mg/kg, about 12 mg/kg, about 15 mg/kg, about 17 mg/kg, about 18 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 90 mg/kg, up to about 100 mg/kg.

The bolus infusion rate or rapid infusion rate for the multidrug combination can vary from about 10 ml/kg/hr, about 12 ml/kg/hr, about 15 ml/kg/hr, about 20 ml/kg/hr, about 25 ml/kg/hr, about 30 ml/kg/hr, about 35 ml/kg/hr, about 40 ml/kg/hr, about 45 ml/kg/hr, about 50 ml/kg/hr, about 55 ml/kg/hr, about 60 ml/kg/hr, about 65 ml/kg/hr, about 70 ml/kg/hr, about 75 ml/kg/hr, about 80 ml/kg/hr, about 85 ml/kg/hr, about 90 ml/kg/hr, about 95 ml/kg/hr, up to about 100 ml/kg/hr.

The bolus duration can be from about 1 minute, about 5 minutes, about 10 minutes, about 20 minutes, about 30 minutes, about 40 minutes, about 50 minutes, about 60 minutes, about 80 minutes, about 100 minutes, about 120 minutes, about 130 minutes, about 140 minutes, about 150 minutes, about 160 minutes, about 170 minutes, about 180 minutes, about 200 minutes, about 210 minutes, about 220 minutes, about 230 minutes, up to about 240 minutes.

The bolus or rapid infusion can be administered as soon as possible after an insult or injury, even before resuscitation. After resuscitation the rapid infusion can be administered about 1 minute, about 5 minutes, about 10 minutes, about 30 minutes, about 1 hour, about 2 hours, about 3 hours, about 5 hours, about 7 hours, about 10 hours, about 12 hours, about 15 hours, about 17 hours, about 20 hours, about 22 hours, up to about 24 hours.

When the following compounds or agents are included in the composition, the dosage rates for components in the multidrug combination for the slower or subsequent infusion are ethanol (about 1 g/kg, about 3 g/kg, about 5 g/kg, about 7 g/kg, about 8 g/kg, about 9 g/kg, about 10 g/kg, about 12 g/kg, about 15 g/kg, about 17 g/kg, about 20 g/kg, about 22 g/kg, up to about 24 g/kg);

vasopressin (about 1 U/kg, about 5 U/kg, about 7 U/kg, about 10 U/kg, about 12 U/kg, about 15 U/kg, about 17 U/kg, about 20 U/kg, about 25 U/kg, about 30 U/kg, about 35 U/kg, about 40 U/kg, about 47 U/kg, about 50 U/kg, about 55 U/kg, up to about 60 U/kg);

lidocaine (0 mg/kg, about 2 mg/kg, about 5 mg/kg, about 7 mg/kg, about 10 mg/kg, about 12 mg/kg, about 15 mg/kg, about 17 mg/kg, about 19 mg/kg, about 20 mg/kg, about 22 mg/kg, up to about 24 mg/kg);

odansetron (0 mg/kg, about 1 mg/kg, about 2 mg/kg, about 2.5 mg/kg, about 3.0 mg/kg, about 3.5 mg/kg, about 4.0 mg/kg, about 4.5 mg/kg, about 5.0 mg/kg, up to about 6.0 mg/kg);

7-OH-DPAT (0 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, up to about 60 mg/kg);

bromocriptine (0 mg/kg, about 5 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 110 mg/kg, up to about 120 mg/kg).

The slow or subsequent infusion rate is from about 0.01 ml/kg/hr, about 0.5 ml/kg/hr, about 1.0 ml/kg/hr, about 1.5 ml/kg/hr, about 2.0 ml/kg/hr, about 2.5 ml/kg/hr, about 3.0 ml/kg/hr, about 3.5 ml/kg/hr, about 4.0 ml/kg/hr, about 4.5 ml/kg/hr, about 5.0 ml/kg/hr, about 5.5 ml/kg/hr, about 6.5 ml/kg/hr, about 7.0 ml/kg/hr, about 7.5 ml/kg/hr, about 8.0 ml/kg/hr, about 8.5 ml/kg/hr, up to about 9.0 ml/kg/hr.

The duration time for the slow or subsequent infusion ranges from about 1 minute, about 10 minutes, about 30 minutes, about 1 hour, about 5 hours, about 7 hours, about 8 hours, about 10 hours, about 12 hours, about 13 hours, about 14 hours, about 15 hours, about 18 hours, about 20 hours, about 24 hours, about 30 hours, about 35 hours, about 40 hours, about 45 hours, about 50 hours, about 55 hours, about 60 hours, about 65 hours, about 70 hours, up to about 72 hours.

When the rapid infusion followed by a slower infusion is used in the treatment of a patient, it is recognized that the multidrug combination may comprise ethanol alone. Additionally any of the components discussed above can be used in combination with ethanol including at least one of a vasoactive compound such as vasopressin, an antiarrhythmic compound such as lidocaine, a serotonin 5-HT$_3$ receptor antagonist such as odansetron, an antioxidant, a vitamin, N-acetylcysteine, and an antihyperglycemic compound such as insulin. Ethanol and any additional agent or agents will be used at the concentrations discussed above and with the infusion rates for the rapid and slow infusion as discussed above.

By "subject" or "patient" is intended an animal, including a mammal, such as a human, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, and cats. In particular embodiments, the subject is a human.

The present invention provides methods for inducing hypothermia in a patient in need thereof. Thus, the methods are useful for treating patients suffering from a clinical insult by administering a therapeutically effective amount of a multidrug combination or composition of the invention before, during, or following the insult.

As used herein, the term "clinical insult" or "clinical event" can refer to any injury, irritation, radiation, physiological derangement, or trauma to a subject that directly or indirectly results in damage to an organelle, cell, tissue or organ in a subject, systemic damage, or death. A clinical insult can also occur at the organellar or cellular level, resulting in cellular damage, which refers to any negative effect on cellular growth or survival, including cell death (e.g., apoptosis, necrosis).

In some embodiments, the insult is of an acute nature. As used herein, an "acute clinical insult" or "acute clinical event" is one which has a relatively rapid onset (e.g., seconds, minutes, hours, days) and is relatively severe, emergent, or life-threatening. The administration of the presently disclosed compositions and multidrug combinations and the hypothermia induced thereby is especially useful for the treatment of acute clinical insults because the general slowing of the metabolic rate and rate of cellular damage that occurs during hypothermia, while being therapeutic in and of itself, also serves to extend the therapeutic window of opportunity following the acute insult during which additional therapeutic treatments can be administered to the patient.

The clinical insult can be systemic or limited to a certain organ (e.g., the brain, heart), tissue, cell type, or organelle. The clinical event can be an exposure to or ingestion of a chemical toxin, radiation, or biological toxin. Non-limiting examples of chemical toxins whose toxicity may be reduced through the presently disclosed methods include nickel, cadmium, selenium, diisopropyl fluorophosphates, chlorpyrifos, and ozone. Non-limiting examples of biological toxins include lipopolysaccharide entotoxemia, bee and cobra venom, and brevetoxin. The clinical event can also be an overdose of a drug. Non-limiting examples of additional clinical insults from which subjects may benefit from the presently disclosed methods include but are not limited to hypoglycemia, hypoxia, uremia, skin burn, hypovolemic shock, vascular ligation, hypergravity, sepsis, an electrocution, a peripheral nerve injury, hepatic encephalopathy, grand mal seizures, hemorrhage, nephropathy, encephalomyelitis, respiratory distress syndrome, invasive surgical procedures (e.g., vascular surgery, neurosurgery), mechanical trauma, radiation, and ischemia. Other clinical insults for which therapeutic hypothermia may be useful can be found in Polderman (2008) *Lancet* 371:1955-1969, which is herein incorporated by reference in its entirety.

The presently disclosed subject matter provides methods for treating a clinical insult. As used herein, the terms "treatment" or "prevention" refer to obtaining a desired pharmacologic and/or physiologic effect. The effect may be prophylactic in terms of completely or partially preventing damage due to a particular clinical insult or sign or symptom resulting therefrom and/or may be therapeutic in terms of a partial or complete reversal of adverse effects due directly or indirectly to a clinical insult. Accordingly, the method "prevents" (i.e., delays or inhibits) and/or "reduces" (i.e., decreases, slows, or ameliorates) and/or reverses the detrimental effects of a clinical insult in the subject receiving the compositions or multidrug combinations of the invention. "Treatment" can also mean preventing the death of the subject or prolonging survival as compared to expected survival if not receiving treatment. Survival can be prolonged by at least about one hour, about two hours, about six hours, about twelve hours, about eighteen hours, about one day, about two days, about three days, about four days, about five days, about six days, about one week, about two weeks, about three weeks, about one month, about 2 months, about 3 months, about 4 months, about 5 months, about 6 months, about 9 months, about a year, or greater following treatment with the compositions or multidrug combinations described herein.

In some embodiments wherein the presently disclosed compositions or multidrug combinations are administered to a subject to treat a clinical insult, the clinical insult comprises an ischemic insult. As used herein, an "ischemic insult" is a clinical insult as defined elsewhere herein that is characterized by or results in ischemia, a condition wherein blood flow to an organ or region of an organ is reduced, which can result in hypoxic and anoxic conditions. Non-limiting examples of ischemic insults include strokes, cardiac arrests, asphyxia, a hanging, traumatic brain injuries, spinal cord injuries, near drowning, heart attacks, acute renal failure, pulmonary embolism, pulmonary infarct, compartment syndrome, an ischemic limb, organ transplant, radiation, and invasive or vascular surgery. Damage due to ischemia can occur during the ischemic episode or after the blood supply has been restored (i.e., reperfusion) to the cell, tissue, or organ. Much of the negative effects of ischemia occur during reperfusion and this damage is often referred to as reperfusion injury or secondary ischemic injury. Reperfusion injury is a result of the innate healing response of the body to the original insult caused by incompletely understood mechanisms. Regardless of the specific mechanisms involved, the end result is edema and disruption of cellular function, which in the case of cerebral edema, can lead to a critical or terminal rise in intracranial pressure, or cell death and loss of brain function. Reoxygenation during reperfusion can also lead to the introduction of a high level of damaging free radicals (Pelligrini-Giampiatro et al. (1990) *J Neurosci* 10:1035-1041).

In some embodiments, the ischemic insult that is treated using the presently disclosed compositions, multidrug combinations, and methods results in cerebral ischemia. As used herein, "cerebral ischemia" refers to a condition wherein blood flow to the entire brain (i.e., global cerebral ischemia) or a region of the brain (i.e., local cerebral ischemia) is reduced. Treatment of cerebral ischemia can result in prolonging the survival of patients administered the presently disclosed compositions or multidrug combinations or can lead to a reduction in neurological deficits due to the enhanced survival of neurons and other vital cells in the brain. The ability of a particular composition, multidrug combination, or method to treat cerebral ischemia or global body ischemia can be tested in an animal model, such as the rodent outcome model of asphyxial cardiac arrest (Katz et al. (1995) *J Cereb Blood Flow Metab* 15:1032-1039) or in the swine model of ischemia described elsewhere herein (see Experimental Example 3).

The development of a fever in a subject that has recently suffered a clinical insult, particularly a neurological injury, can lead to an increased duration of hospitalization, a higher mortality rate, and a generally worse outcome (Polderman (2008) *Lancet* 371:1893-1895; Greer (2008) *Stroke* 39:3029-3035). It is estimated that approximately 30% of patients in intensive care units develop an intractable fever (Polderman (2008) *Lancet* 371:1893-1895; Greer (2008) *Stroke* 39:3029-3035). The presently disclosed methods of treating a clinical insult through the administration of a regulated hypothermic compound and at least one of a vasoactive compound, an antioxidant, an antiarrhythmic compound, a vitamin, and an antihyperglycemic compound have the added benefit of preventing or reducing a fever that may develop in the subject following the clinical insult that would ordinarily compromise the recovery of the subject from the insult.

As used herein, the term "fever", which is also referred to herein as "hyperthermia" refers to a condition in a temperature-regulating organism where the organism's core body temperature is above the normal core body temperature set point for the organism. In some embodiments, a hyperthermic organism has a core body temperature that is at least about 1° C., about 2° C., about 3° C., about 4° C., about 5° C., about 6° C., about 7° C., about 8° C., about 9° C., about 10° C., or warmer than the normal core body temperature for the organism.

In some organisms, the normal core body temperature for an organism is about 37° C. and the hyperthermic organism has a core body temperature of greater than 37° C., including but not limited to, about 37.5° C., about 38° C., about 38.5° C., about 39° C., about 39.5° C., about 40° C., about 40.5° C., about 41° C., about 41.5° C., about 42° C., about 42.5° C., about 43° C., about 43.5° C., about 44° C., about 44.5°, about 45° C., about 45.5° C., about 46° C., about 46.5° C., about 47° C., or warmer.

Further, the presently disclosed methods for treating a clinical insult also serve to reduce the incidence of shivering that can often occur during hypothermia, treatment of fever, or following a particularly traumatic clinical insult or surgery. As used herein, the term "shivering" refers to an essentially involuntary, oscillatory muscular activity that presents as a tremor. Shivering can cause discomfort in the subject, lead to increased oxygen consumption, increased carbon dioxide production, increased catecholamine release, increased glucose levels, increased cardiac output, tachycardia, hypertension, elevated intracranial pressure, and increased mortality (Crossley (1992) *Anaesthesia* 47:193-195). Thus, for the purposes of the present invention, shivering can be considered a clinical insult and the presently disclosed compositions and multidrug combinations can also be used to reduce or prevent shivering that can occur, for example, following the administration of general anesthesia compounds that result in hypothermia. Non-limiting examples of general anesthesia compounds that can lead to hypothermia upon administration include isoflurane, propofol, etomidate, ketamine, sevoflurane, midazolam, barbiturates including but not limited to methohexital and thiopental, and benzodiazepines including but not limited to midazolam and diazepam. The administration of general anesthetics can lead to the development of nonregulated hypothermia in patients. Unlike anesthetics, the administration of the multidrug combinations of the invention resulting in regulated hypothermia reduced the set point temperature of the patient. The administration of the presently disclosed compositions and multidrug combinations resulting in regulated hypothermia reduces the thermoregulatory set-point temperature in the patient, which serves to reduce or prevent shivering that can otherwise occur during hypothermia.

Methods for treating a clinical insult can include administering a therapeutically effective amount of any one of the presently disclosed compositions or multidrug combinations. In some embodiments, the method comprises administering a therapeutically effective amount of a regulated hypothermic compound and at least one of a vasoactive compound, an antioxidant, an antiarrhythmic compound, a vitamin, and an antihyperglycemic compound. In general, the administration of the multidrug combination is more effective in treating a clinical insult than the regulated hypothermic compound alone.

As used herein, a "therapeutically effective amount" or "dose" is an amount sufficient to effect a beneficial or desired therapeutic, clinical or biochemical result. An effective amount can be administered one or more times, but is administered in an amount sufficient to elicit the desired therapeutic effect. A therapeutically effective amount of the regulated hypothermic compound of the multidrug combinations disclosed herein is an amount sufficient to induce therapeutic hypothermic temperatures and an amount sufficient to induce regulated hypothermia, wherein the thermoregulatory set-point temperature is reduced. According to the presently disclosed methods, the subjects that have been administered the compositions or multidrug compositions disclosed herein are allowed to reach hypothermic temperatures. Therefore, no external heat is applied to the subjects before, during, or after the administration of the composition or multidrug combination nor are other measures taken to maintain normothermic temperatures.

It is recognized that the therapeutically effective amount of the drug components may vary depending on the age, weight, and sex of the subject being treated as well as the severity and nature of the insult being treated.

Acute ingestion of ethanol above 10 g/kg is considered toxic (Gable (2004) *Addiction* 99(6):686-696), although the toxic level of ethanol administered over a longer period of time is not well studied. Therefore, in some of those embodiments wherein the regulated hypothermic compound comprises ethanol, between about 0.75 g/kg and about 10 g/kg of ethanol is administered to the subject, including but not limited to about 0.75 g/kg, about 0.8 g/kg, about 0.9 g/kg, about 1.0 g/kg, about 1.1 g/kg, about 1.2 g/kg, about 1.3 g/kg, about 1.4 g/kg, about 1.5 g/kg, about 1.6 g/kg, about 1.7 g/kg, about 1.8 g/kg, about 1.9 g/kg, about 2.0 g/kg, about 2.1 g/kg, about 2.2 g/kg, about 2.3 g/kg, about 2.4 g/kg, about 2.5 g/kg, about 2.6 g/kg, about 2.7 g/kg, about 2.8 g/kg, about 2.9 g/kg, about 3.0 g/kg, about 3.1 g/kg, about 3.2 g/kg, about 3.3 g/kg, about 3.4 g/kg, about 3.5 g/kg, about 3.6 g/kg, about 3.7 g/kg, about 3.8 g/kg, about 3.9 g/kg, about 4.0 g/kg, about 5 g/kg, about 6 g/kg, about 7 g/kg, about 8 g/kg, about 9 g/kg, and about 10 g/kg. In certain embodiments about 2.0 g/kg of ethanol is administered to the subject.

In certain embodiments wherein a subject is administered a vasoactive compound comprising vasopressin, vasopressin is administered to the subject in an amount ranging between about 0.001 U/kg and about 10 U/kg, including but not limited to about 0.001 U/kg, about 0.002 U/kg, about 0.003 U/kg, about 0.004 U/kg, about 0.005 U/kg, about 0.01 U/kg, about 0.05 U/kg, about 0.075 U/kg, about 0.1 U/kg, about 0.2 U/kg, about 0.3 U/kg, about 0.4 U/kg, about 0.5 U/kg, about 0.6 U/kg, about 0.7 U/kg, about 0.8 U/kg, about 0.9 U/kg, about 1.0 U/kg, about 1.1 U/kg, about 1.2 U/kg, about 1.3 U/kg, about 1.4 U/kg, about 1.5 U/kg, about 1.6 U/kg, about 1.7 U/kg, about 1.8 U/kg, about 1.9 U/kg, about 2.0 U/kg, about 3.0 U/kg, about 4.0 U/kg, about 5.0 U/kg, about 6.0 U/kg, about 7.0 U/kg, about 8.0 U/kg, about 9.0 U/kg, and about 10.0 U/kg. In other embodiments, vasopressin is administered in an amount ranging between about 0.075 U/kg and about 10 U/kg, in particular embodiments, about 0.75 U/kg of vasopressin is administered to the subject, and in other embodiments about 0.2 U/kg of vasopressin is administered to the subject.

When utilized, the antioxidant compound can comprise N-acetylcysteine, which in some embodiments can be administered to a subject in amounts ranging between about 10 mg/kg and about 1200 mg/kg, including but not limited to about 10 mg/kg, 20 mg/kg, 30 mg/kg, 40 mg/kg, 50 mg/kg, about 75 mg/kg, about 100 mg/kg, about 125 mg/kg, about 150 mg/kg, about 175, about 200, about 225, about 250, about 275, about 300 mg/kg, about 400 mg/kg, about 500 mg/kg, about 600 mg/kg, about 700 mg/kg, about 800 mg/kg, about 900 mg/kg, about 1000 mg/kg, about 1100 mg/kg, and about 1200 mg/kg. In certain embodiments, between about 50 mg/kg and about 300 mg/kg, and in particular embodiments, about 150 mg/kg or about 92 mg/kg of N-acetylcysteine is administered to the subject.

In those embodiments wherein an antiarrhythmic compound is administered to a subject, the antiarrhythmic compound can comprise lidocaine, which can be administered to the subject in an amount ranging between about 0.1 mg/kg and about 10 mg/kg, including but not limited to about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, and about 10 mg/kg. In particular embodiments, between about 1 mg/kg and about 4 mg/kg, and in certain embodiments about 1 mg/kg or about 2 mg/kg of lidocaine is administered to subjects. In particular during the rapid infusion or bolus administration about 2 mg/kg of lidocaine is administered to subjects.

When a vitamin is utilized, the vitamin can comprise folate, thiamine, or both folate and thiamine. Folate can be administered to a subject in an amount ranging between about 0.1 mg/kg and about 10 mg/kg, including but not limited to about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, and about 10 mg/kg. In particular embodiments, about 0.25 mg/kg of folate is administered to the subject. In certain embodiments, thiamine can be administered in an amount ranging between about 0.1 mg/kg and about 10 mg/kg, including but not limited to about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, and about 10 mg/kg. In particular embodiments, about 5 mg/kg thiamine is administered to the subject during the rapid infusion or bolus.

In some of those embodiments wherein an antihyperglycemic compound is utilized, the antihyperglycemic compound comprises insulin, which can be administered to the subject in an amount ranging between about 0.05 U/kg and about 10 U/kg, including but not limited to, about 0.05 U/kg, about 0.1 U/kg, about 0.25 U/kg, about 0.5 U/kg, about 0.75 U/kg, about 1 U/kg, about 2 U/kg, about 3 U/kg, about 4 U/kg, about 5 U/kg, about 6 U/kg, about 7 U/kg, about 8 U/kg, about 9 U/kg, and about 10 U/kg. In certain embodiments, about 0.25 U/kg of insulin is administered to the subject during the rapid infusion or bolus.

In some of those embodiments wherein a therapeutically effective amount of a regulated hypothermic compound and a vasoactive compound are administered to a subject, hypothermia is induced in said subject in a reduced amount of time in comparison to administering the regulated hypothermic compound alone. Therefore, in some of these embodiments, the amount of time required to reach a particular target hypothermic temperature is reduced by between about 5 minutes and about 4 hours, including but not limited to about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 70 minutes, about 80 minutes, about 90 minutes, about 100 minutes, about 110 minutes, about 120 minutes, about 150 minutes, about 180 minutes, about 210 minutes, and about 240 minutes in comparison to administering the regulated hypothermic compound alone. The target hypothermic temperature can comprise a temperature that is between about 2° C. and about 4° C. below the normal core body temperature of the subject. In a subject that has a normal core body temperature of about 37° C., the target hypothermic temperature can comprise between about 33° C. and about 35° C. and in some embodiments is about 33° C.

When a rapid infusion followed by a slow infusion is used for administration of the multidrug combination, a regulated hypothermic compound and a vasoactive compound can be administered to a subject to induce regulated hypothermia to prevent or reduce shivering or other physiological warming responses associated with hypothermia. For example, patients that have received general anesthesia frequently experience hypothermia. These patients can be administered a regulated hypothermic compound and a vasoactive compound in order to induce regulated hypothermia and reduce the thermoregulatory set-point temperature in these patients, which serves to minimize the physiological warming responses including shivering in these patients. In some of these embodiments, the amount of time required to reduce the thermoregulatory set-point temperature and therefore, reduce physiological warming responses (e.g., shivering) after administration of a regulated hypothermic compound and a vasoactive compound hypothermia is reduced in comparison to administering the regulated hypothermic compound alone. In some of these embodiments, the amount of time required to reduce or prevent physiological warming responses (e.g., shivering) is reduced by between about 5 minutes and about 2 hours, including but not limited to about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 70 minutes, about 80 minutes, about 90 minutes, about 100 minutes, about 110 minutes, and about 120 minutes, in comparison to administering the regulated hypothermic compound alone.

The presently disclosed compositions or multidrug combinations can be administered to a subject in a single dose (e.g., intravenous bolus) or in multiple doses. As discussed, a two phase method of administration of an intravenous rapid infusion followed by a slow infusion is useful in some instances. In some of these embodiments, the subject can experience hypothermic temperatures (and a reduction in the set-point temperature) for a period of time ranging from between about 10 minutes and about 12 hours, including but not limited to about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 2 hours, about 3 hours, about 4 hours, about 5 hours, about 6 hours, about 7 hours, about 8 hours, about 9 hours, about 10 hours, about 11 hours, and about 12 hours. In certain embodiments, a single administration of the presently disclosed compositions or multidrug combinations can result in hypothermia for at least about 8 hours.

The time it requires to lower body temperature and the period of time which the hypothermic state is maintained after a single dose of the composition or multidrug combination (i.e., a bolus or period of rapid infusion), can be prolonged through the continued administration of the slow infusion of the multidrug combination. In some embodiments, the period of time in which the hypothermic state is maintained after a single administration of rapid infusion (e.g., intravenous bolus) of the composition or multidrug combination can be extended by about an hour to about 24 hours, including but not limited to about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, and about 24 hours.

While compositions comprising different concentrations of the multidrug combination can be administered during the two phase method of administration, one advantage of the present invention is that the same compositions that are prepared for the rapid infusion (bolus) can be used for the subsequent infusion. That is the concentration of the multidrug combination delivered to the patient can be controlled by the infusion rate. In this embodiment, a single composition can be prepared and used for the rapid infusion followed by subsequent infusion at a slower rate. This method of administration, a rapid infusion or bolus followed by a slower infusion is able to induce a hypothermic state in a short amount of time and to extend the time that the patient is in the hypothermic state for an extended period of time.

An extended period of regulated hypothermia is useful for those conditions and clinical insults that do not readily respond to forced hypothermia. For these conditions, a continuous slow infusion of the presently disclosed compositions or multidrug combinations, particularly those comprising an antioxidant, can be administered. In some embodiments, continuous or extended administration (e.g., intravenous infusion) of the presently disclosed compositions or multidrug combinations can result in a state of hypothermia that can last from between about 1 hour and about 12 hours, including but not limited to about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 48 hours, about 72 hours, and in some embodiments longer.

The addition of an antiarrhythmic compound and/or vasoactive agent to the composition or multidrug combination that is administered continuously or for an extended period of time (e.g., slow intravenous infusion) can extend the hypothermic state. In some embodiments, the addition of an antiarrhythmic compound and/or vasoactive agent extends the hypothermic state by about an hour to about 60 hours, including but not limited to about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 24 hours, about 30 hours, about 36 hours, about 40 hours, about 44 hours, about 48 hours, about 50 hours, about 52 hours, about 54 hours, about 56 hours, about 58 hours, and about 60 hours. With a continuous infusion of the presently disclosed compositions or multidrug combinations comprising an antiarrhythmic compound and/or vasoactive agent, the hypothermic state can be maintained for an indefinite period of time.

A regulated hypothermic compound and an antiarrhythmic compound and/or vasoactive agent can be administered to a subject by rapid infusion to induce regulated hypothermia and by slow infusion to maintain the regulated hypothermia (reduced set-point temperature and reduced core body temperature) for an extended period of time to prevent or reduce shivering or other physiological warming responses associated with hypothermia (e.g., post-anesthesia shivering).

In some of the embodiments wherein an ischemic insult is being treated in a subject, the ischemia occurs in an organelle, cell, tissue, or organ of the subject secondary to the removal of the cell, tissue, or organ from the subject or from its normal physiological site. In these embodiments, the administration of a composition or multidrug combination of the invention is administered to the subject prior to the removal of the cell, tissue, or organ from its normal physiological site. In some embodiments, the cell, tissue, or organ is transplanted to another site (i.e., acceptor site) within the subject from which it was removed or it is transplanted to another subject (i.e., acceptor subject).

The induction of hypothermia in the subject from which the organelle, cell, tissue, or organ was removed prior to its removal pre-cools the organelle, cell, tissue, or organ, reduces the metabolic rate of the organelle, cell, tissue, or organ, and protects the organelle, cell, tissue, or organ from cellular damage, thus preserving the cell, tissue, or organ that is destined for in situ resuscitation or the transplant. In some embodiments, the administration of a composition or multidrug combination of the invention to a subject prior to the removal of a cell, tissue, or organ destined for a transplant increases the period of time between removal of the cell, tissue, or organ, and its transplantation into the new acceptor subject or acceptor site that allows for a successful transplantation.

Any of the presently disclosed compositions or multidrug combinations can be administered before, during, or following a clinical insult, which in some embodiments comprises an ischemic insult. In each of the embodiments discussed herein, it is recognized that the multidrug combinations can be administered by the rapid infusion or bolus followed by a slow infusion. In certain embodiments, the composition or multidrug combinations can be administered between about 1 minute and about 24 hours before the clinical insult, including but not limited to about 1 minute, about 2 minutes, about 3 minutes, about 4 minutes, about 5 minutes, about 10 minutes, about 15 minutes, about 20 minutes, about 30 minutes, about 45 minutes, about 60 minutes, about 90 minutes, about 120 minutes, about 150 minutes, about 180 minutes, about 4 hours, about 5 hours, about 6 hours, about 7 hours, about 8 hours, about 9 hours, about 10 hours, about 12 hours, about 15 hours, about 20 hours, about 22 hours, and about 24 hours before the clinical insult. In some embodiments, the composition or multidrug combination is administered between about 20 minutes and about 60 minutes before the clinical insult.

In other embodiments, one of the presently disclosed compositions or multidrug combinations is administered during the clinical insult. In still other embodiments, one of the presently disclosed compositions or multidrug combinations is administered to the subject following the insult. In some of these embodiments, the composition or the multidrug combination is administered within about 1 minute to about 72 hours following the clinical insult, including but not limited to, about 1 minute, about 2 minutes, about 3 minutes, about 4 minutes, about 5 minutes, about 10 minutes, about 15 minutes, about 20 minutes, about 30 minutes, about 45 minutes, about 60 minutes, about 90 minutes, about 120 minutes, about 150 minutes, about 180 minutes, about 4 hours, about 5 hours, about 6 hours, about 7 hours, about 8 hours, about 9 hours, about 10 hours, about 12 hours, about 15 hours, about 20 hours, about 22 hours, about 24 hours, about 30 hours, about 36 hours, about 40 hours, about 48 hours, about 50 hours, about 56 hours, about 60 hours, about 66 hours, about 70 hours, and about 72 hours following the clinical insult. In certain embodiments, one of the presently disclosed compositions or multidrug combinations is administered within about 5 minutes to about 8 hours following the clinical insult. In particular embodiments, the composition or the multidrug combination is administered between about 5 minutes and about three hours following the clinical insult. The period of time between an acute insult, such as a cardiac arrest, and the administration of the compositions or multidrug combinations disclosed herein is especially critical. Thus, in some embodiments, in order to minimize permanent injuries, the compositions or multidrug combinations are administered as soon as possible, including within about 5 minutes, about 10 minutes, about 30 minutes, about one hour to about eight hours of the acute insult.

In those embodiments wherein the clinical insult comprises an ischemic insult, a presently disclosed composition, multidrug combination, or ethanol alone can be administered following the ischemic insult or during or following reperfusion (e.g., due to resuscitation). In some of these embodiments, the composition, combination therapy, or ethanol is administered between about 1 minute and about 24 hours following reperfusion, including but not limited to about 1 minute, about 2 minutes, about 3 minutes, about 4 minutes, about 5 minutes, about 10 minutes, about 15 minutes, about 20 minutes, about 30 minutes, about 45 minutes, about 60 minutes, about 90 minutes, about 120 minutes, about 150 minutes, about 180 minutes, about 4 hours, about 5 hours, about 6 hours, about 7 hours, about 8 hours, about 9 hours, about 10 hours, about 12 hours, about 15 hours, about 18 hours, about 20 hours, about 22 hours, and about 24 hours following reperfusion.

It should be noted that the presently disclosed methods, compositions, and multidrug combinations can be used in combination with other therapeutic interventions, including other pharmaceuticals or methods that are effective in treating the clinical insult. In some embodiments, the presently disclosed methods, compositions, and multidrug combinations can be used in combination with forced hypothermic methods, such as an intravenous infusion of cooled solutions, endovascular cooling or external cooling methods or artificially inducing sweating by moistening the skin. Further, thrombolytics, such as tissue plasminogen activator can be administered to the subject to which the presently disclosed compositions or ethanol alone are administered to treat ischemic insults (e.g., stroke, myocardial infarction).

Toxicity and therapeutic efficacy of the presently disclosed compositions and multidrug combinations can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the presently disclosed methods, the therapeutically effective dose can be formulated in animal models to achieve a circulating plasma concentration range that includes the $IC_{50}$ (i.e., the concentration of the test compound which achieves a half-maximal inhibition of symptoms). Such information can be used to more accurately determine useful doses in humans. Levels in plasma can be measured, for example, by high performance liquid chromatography.

The presently disclosed compositions and multidrug combinations can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, and the like. Further, as described above an initial bolus or rapid infusion can be administered followed by a slower or subsequent continuous infusion for about 4 to about 24 hours. The skilled artisan will appreciate that certain factors can influence the dosage and timing required to effectively treat a subject, including but not limited to the type of clinical insult, the severity of the symptoms resulting from the clinical insult, previous treatments, the general health and/or age of the subject, and other diseases or unwanted conditions present. Generally, treatment of a subject can include a single treatment (e.g., an intravenous, intramuscular, or subcutaneous bolus) or, in many cases, can include a series of treatments such as a bolus followed by at least one incident of a slower infusion or continuous infusion.

It is understood that appropriate doses of a compound depend upon its potency and can optionally be tailored to the particular recipient, for example, through administration of increasing doses until a preselected desired response is achieved. It is understood that the specific dose level for any particular animal subject can depend on a variety of factors including the activity of the specific compound employed, the age, body weight, general health, gender, genetic makeup, and diet of the subject, the time of administration, the route of administration, the rate of administration, the volume of administration, the rate of excretion, any drug combination, and the degree of the activity to be modulated.

In general, the composition or components of the multidrug combination are administered to a subject, wherein the composition or components of the multidrug combination are at a normal physiological temperature (e.g., about 37° C.), at room temperature (e.g., about 20° C. to about 30° C.), or at a refrigerated temperature (e.g., about 0° C. to about 5° C.). Thus, in some embodiments, the temperature of the composition or components of the multidrug combination that are administered to a subject ranges from about 0° C. to about 37° C.

It is to be noted that the term "a" or "an" entity refers to one or more of that entity; for example, "a drug" is understood to represent one or more drugs. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The following examples are offered by way of illustration and not by way of limitation.

EXPERIMENTAL

General Overview

Data presented herein (see Experimental Examples 1-2) demonstrate that the administration of ethanol-comprising multidrug combinations after total body ischemia in a rodent model of asphyxial cardiac arrest can result in a drastic improvement in survival and nearly complete protection of all organelles, cells, tissues, and organs (brain, heart, kidney, lungs, intestines, etc.) following reperfusion.

The outcome model of asphyxial cardiac arrest in rats that was used in these studies was developed to study clinically realistic focal and global body ischemia and hypoxic-ischemic reperfusion injury (Katz et al. (1995) J Cereb Blood Flow Metab 15:1032-1039). This rodent model produces global hypoxic-ischemic damage to all organs with a phenotype very similar to that in humans, including the presentation of post resuscitative encephalopathy (coma) and reperfusion disease, histological damage and spatial learning and memory deficits (Katz et al. (1995) *J Cereb Blood Flow Metab* 15:1032-1039; Katz et al. (2001) *Acad Emerg Med* 8:1115-1121; Radovsky et al. (1997) *Toxicol Pathol* 25:500-505). Reperfusion disease from asphyxial cardiac arrest in rats in this model also causes selective ischemic cell vulnerability in the hippocampus and other brain regions (Katz et al. (1995) *J Cereb Blood Flow Metab* 15:1032-1039; Radovsky et al. (1997) *Toxicol Pathol* 25:500-505) as also occurs with focal ischemia. Rats in this model have a 20% long term survival rate, approximating that in humans experiencing out of hospital witnessed cardiac arrests (Hallstrom et al. (2007) *Resuscitation* 74:418-426; Hess et al. (2007) *Resuscitation* 72:200-206). The model also produces a distribution of histological damage throughout the brain similar to humans with asphyxial cardiac arrest (Kinney et al. (1994) *N Engl J Med* 330:1469-1475).

An important limitation for other rodent models is their failure to produce coma or predict therapeutic outcome in clinical trials (Bircher and Abramson (1984) *Am J Emerg Med* 2:371). The outcome model of asphyxial cardiac arrest in rats provides some advantages over other rodent models of global brain ischemia in that it produces hypoxic-ischemic injury to all organs, not just the brain. The rats also experience post ischemic encephalopathy (coma) and damage from reperfusion disease (Katz et al. (1995) *J Cereb Blood Flow Metab* 15:1032-1039; Negovsky and Gurvitch (1995) *Resuscitation* 30:23-27; Safar (1986) *Circulation* 74: IV138-IV153). A unique feature of the model is it discriminates candidate therapeutics that have failed to translate to improved neurological outcome in clinical trials.

The rat outcome model of asphyxial cardiac arrest also predicts the beneficial effects and limitations of forced hypothermia observed in clinical trials of hypoxic-ischemic brain injury (Kim et al. (2007) *Circulation* 115:3064-3070; Shankaran et al. (2005) *N Engl J Med* 353:1574-1584). The model is able to simulate the timing and methods currently available to induce forced hypothermia in humans. Therefore, the results presented herein demonstrate that the administration of ethanol alone (at certain doses) and in combination with vasopressin and at least one of lidocaine, odansetron, N-acetylcysteine, insulin, folate, or thiamine is capable of reducing mortality or neurological deficits after ischemia in the rat outcome model of asphyxial cardiac arrest strongly suggests that similar methods would improve patient outcome after ischemia.

Further, in a large animal (swine) model of asphyxial cardiac arrest, the administration of ethanol-comprising multidrug combinations reduces plasma and CSF levels of neuron specific enolase, which is a marker of brain injury (see Experimental), providing further evidence that ethanol and the presently disclosed ethanol-comprising drug combinations are effective at treating acute ischemia, especially as it relates to brain and heart injury. While not being bound by any theory or mechanism of action, it is believed that the decrease in mortality and neuroprotection in the ischemic rat and swine models afforded by ethanol and ethanol-comprising multidrug combinations is due to the induction of regulated hypothermia. Additional experiments demonstrate the effectiveness of the administration of the multidrug combination in at least a two phase administration: a bolus or rapid infusion step; followed by a subsequent or slow infusion. This two phase method of administration rapidly induces hypothermia and maintains the hypothermic state. The slow infusion after the administration of a bolus or a period of rapid infusion prolongs duration of the hypothermic state. The results indicate that the rate of infusion can control the reduction and maintenance of body temperature. Therefore, one of skill in the art can titrate the concentration and rate of infusion to reach the desired temperature.

Methods for Examples 1 and 2

Rat Model of Asphyxial Cardiac Arrest

The outcome model of asphyxial cardiac arrest in rats was used for these studies and has been described previously (Katz et al. (1995) *J Cereb Blood Flow Metab* 15:1032-1039). Briefly, rats were anesthetized with 4% isoflurane, intubated and mechanically ventilated, anesthesia was titrated and vessel catheters inserted. Cardiac arrest was induced by apneic asphyxia with chemical paralysis (vecuronium 2 mg/kg) and discontinuation of ventilation. After 10 minutes of asphyxial cardiac arrest, rats were resuscitated with mechanical ventilation, 100% $O_2$, epinephrine (0.005 mg/kg) and chest compressions. Rats were extubated two hours after resuscitation and placed in a humidity and temperature controlled incubator. Rats were sacrificed by an overdose (5%) of inhaled isoflurane and then perfusion fixed with 100 ml of 4% paraformaldehyde at a perfusion pressure of 100 mmHg. Multiple coronal sections (10 μm thickness) of the brain (Paxinos et al. (1995) *J Neurosci Methods* 13:139-143) were cryosectioned for future immunostaining and histological evaluation.

Temperature Monitoring:

Surgical procedures are performed with titrated (1-2.5%) inhaled isoflurane anesthesia. The abdomen is prepped and draped in the usual fashion and the abdomen incised for the laparotomy. A telemetric temperature G2 probe (MiniMitter, Sun River, Oreg.) is sutured to the inside posterior wall of the right peritoneum adjacent to the vena cava with the superior pole of the probe at the level of the apex of the kidney. The abdominal incision is approximated with prolene sutures and the rats are allowed to recover for at least three days before asphyxial cardiac arrest. Temperature is telemetrically monitored and maintained at the target temperatures with a cooling and warming system controlled by a servo-feedback system from signals obtained every 5 seconds from the abdominal temperature probe.

Neurological Deficit (ND) Score:

A neurological deficit score (NDS), modified for rats, performed daily for three days after return of spontaneous circulation (ROSC) correlates with the duration of asphyxia and is predictive of survival, similar to the 72-hour neurological exam in humans (Maramattom and Wijdicks (2005) *Neurologist* 11:234-243).

The total ND score is composed of 5 components as outlined below. A normal rat has a ND score of 0% and a brain-dead rat has an ND score of 100% (Katz et al. (1995) *J Cereb Blood Flow Metab* 15:1032-1039).

1. General Behavior

| Consciousness | Normal (0) | Comatose (20) |
| Respirations | Normal (0) | Labored (20) |

2. Cranial Nerve Reflexes

| Olfactory (sniffing) | Present (0) | Absent (4) |
| Vision | Present (0) | Absent (4) |
| Corneal reflex | Present (0) | Absent (4) |
| Whisker movement | Present (0) | Absent (4) |
| Hearing | Present (0) | Absent (4) |

3. Motor Function

| Legs/tail movement | Normal (0) | Stiff (5) | Absent (10) |

4. Sensory Function

| Legs/tail | Present (0) | Absent (10) |

5. Coordination

| Balance beam | Normal (0) | Abnormal (5) | Absent (10) |
| Placing test | Normal (0) | Abnormal (5) | Absent (10) |
| Righting reflex | Normal (0) | Abnormal (5) | Absent (10) |
| Stop at edge | Normal (0) | Abnormal (5) | Absent (10) |

Morris Water Maze:

At the indicated time after resuscitation, rats were assessed for performance in a Morris Water Maze. The maze consists of a six foot diameter round pool, filled with water (26° C.) to a depth of 20 cm, one cm above an 11 cm diameter clear glass escape platform. The escape platform is invisible to the swimming rat and placed in the northeast quadrant floor of the pool for 4 out of 5 trials. The pool has large visible and distinct geometric shapes placed in a north, south, east and west distribution on the side of the pool wall so that a swimming rat can easily visualize the orientation markers and use them to triangulate the location of the hidden platform. Rats were initially placed in the pool (without the escape platform) for two minutes to become acclimated to the new swimming environment. They were then placed on the escape platform for 30 seconds to allow for orientation in the pool. The rats swim in the pool with a visible platform on the first day to assure normal swimming and vision. Next, the rats were randomly placed in each of the four geographic outer regions of the pool and their travel path, swim speed, time in a quadrant and time required to locate the hidden platform (latency time) was recorded with a visual tracking system (EthoVision). Rats performed four swim trials on each day with the escape platform in the same location and a fifth trial (probe trial) with no escape platform. Rats were allowed to swim a maximum of two minutes or until they located the platform for each trial. A two minute rest period in a temperature controlled environment (to avoid hypothermia) was provided between each trial.

An updated Morris Water Maze procedure was performed for the most recent group of rats. On trial day 1, after the initial acclimation swim, rats perform four swimming trials with a visible platform to confirm adequate swimming and normal vision. On trial days 2-6 three swimming trials are performed with the hidden platform present and the fourth trial is conducted with the platform removed. This modification was performed to improve the quality of the probe trial.

Example 1

Administration of Ethanol-Comprising Multidrug Combinations Provide Partial to Complete Neuroprotection in a Rat Model of Cardiac Arrest Asphyxial cardiac arrest was used as the acute insult in these studies as this type of cardiac arrest may benefit most from regulated hypothermia because the therapeutic window is narrow, as demonstrated in pilot experiments. Rats underwent ten minutes of asphyxial cardiac arrest and resuscitation. Five minutes after the return of spontaneous circulation (ROSC), rats were administered 15 ml/kg of iced normal (0.9%) saline (5° C.) (forced hypothermia) or half of the indicated treatment (at room temperature, 21° C.) intravenously over 20 minutes. The first infusion was followed immediately by a second 20-minutee infusion (15 ml/kg) with iced saline (5° C.) for the forced hypothermia group or the second half of the indicated treatment (at 21° C.).

When the second infusion was completed (45 minutes after ROSC), the forced hypothermia rats were placed in air-conditioned chambers (12° C.) controlled through feedback with the abdominal telemetry unit that allows for the maintenance of a hypothermic core temperature of 33° C. for 24 hrs. Temperature was monitored with a telemetric probe implanted in the abdomen. Trunk instead of brain temperature was monitored because it allows for translation to monitoring methods used in clinical trials ((2002) *N Engl J Med* 346:549-556; Bernard et al. (2002) *N Engl J Med* 346:557-563).

Forty-five minutes after ROSC, the rats that had been administered iced saline (the forced hypothermia treatment) were externally cooled through the application of cooling pads. This time point was chosen for the transition from iced saline to external cooling as that approximates the time when patients would have access to cooling equipment available in the Emergency Department ((2002) *N Engl J Med* 346:549-556; Bernard et al. (2002) *N Engl J Med* 346:557-563; Davis et al. (2007) *Resuscitation* 74:44-51; Haugk et al. (2007) *Resuscitation* 75:76-81). External cooling was chosen over endovascular cooling for this step because of the technical limitation of applying endovascular cooling in rodents. Although endovascular cooling may have some advantages over external cooling for providing tight control of body temperature, there is a paucity of evidence that endovascular cooling by itself improves outcome better than external cooling (Hoedemaekers et al. (2007) *Crit. Care* 11:R91; Jordan and Carhuapoma (2007) *J Neurol Sci* 261:35-38).

Twenty-four hours after induction of hypothermia, rats in the forced hypothermia group were housed at a thermoneutral ambient temperature of 30° C. that provides a consistent rewarming rate of about 0.25° C./hr after forced hypothermia (Romanovsky et al. (2002) *J Appl Physiol* 92:2667-2679). Rats treated with the multidrug combinations spontaneously rewarmed to normothermia without the addition of heat. Without being bound by any theory or mechanism of action, it is believed that the rats in the regulated hypothermia combination therapy group rewarmed to normothermia because the normal setpoint (37° C.) was restored when the drug was cleared from the body by either liver or renal routes. When the setpoint was restored, metabolism and thus, endogenous heat production is restored to reach normothermia. We observed no shivering during the restoration of normothermia after regulated hypothermia. Rats were then maintained at ambient temperature (e.g., 20° C. to about 25° C.) until sacrifice. An ND score was performed daily by an investigator blinded to interventions.

The effect of ethanol alone on body temperature was measured. A dose of about 0.75 g/kg is the minimum dose of ethanol able to reliably induce hypothermia. This effect plateaus at 3 g/kg of ethanol and higher doses of ethanol do not further lower the temperature. A temperature of about 33° C. is reached by about 30 to 40 minutes and is maintained during infusion.

The effect of 6 minutes, 8 minutes, or 10 minutes of asphyxial cardiac arrest on the neurological deficit score in rats (n=10) measured after 24 hours, 48 hours, or 72 hours after resuscitation in the absence of any hypothermic treatment. The results clearly demonstrated that the longer the time of asphyxial cardiac arrest the higher the NDS score indicating greater neural injury.

The effects of forced hypothermia or regulated hypothermia induced with ethanol at 0.5 g/kg (low dose), 0.75 g/kg (low/medium dose), 1 g/kg (medium dose), and 3 g/kg (high dose); along with 1 mg/kg of lidocaine, 10 mg/kg of N-acetylcysteine, 1 mg/kg of thiamine, and 0.3 mg/kg folate on the neurological deficit score scored 24 hours, 48 hours, and 72 hours after resuscitation from asphyxial cardiac arrest (n=6 for each treatment group) was measured. Rats that had been administered ethanol at a low/medium dose or a dose of 1 g/kg, along with the other components exhibited a significant reduction in neurological deficits 72 hours after ROSC.

Rats that had undergone asphyxial cardiac arrest for 10 minutes or a sham surgery and treated as above were tested in the Morris Water Maze on days 11-15 after ROSC. Sham rats provided a baseline for swimming performance in the Morris Water Maze. 15 days after ROSC, rats that had undergone asphyxial cardiac arrest and treated with 1 g/kg of ethanol along with the other components of the cocktail performed nearly identically to the sham animals.

Example 2

Effects of Various Ethanol-Comprising Multidrug Combinations on Survival and Neurological Deficits in the Rat Model of Asphyxial Cardiac Arrest The rat outcome model of asphyxial cardiac arrest was used to test each of the components of the cocktail to determine the effects of the components on NDS and performance in the Morris Water Maze. Rats undergoing forced hypothermia and rats maintained under normothermic conditions (with 0.5 U/kg vasopressin administered) served as controls. Raw survival and NDS data is shown in Table 1 and Table 2 provides a summary of the survival and NDS data.

Administration of ethanol alone (under normothermic conditions) at doses of 1 g/kg, 1.5 g/kg, and 2 g/kg were able to enhance survival of the rats about 1.5- to 3-fold and reduced the neurological deficit score at 72 hours after resuscitation. Vasopressin alone (under normothermic conditions) also enhanced survival approximately 3-fold and reduced neurological deficits 72 hours after resuscitation. The combination of ethanol (at 2 g/kg) and vasopressin (at 0.75 U/kg), when rats were allowed to become hypothermic, had a synergistic effect on survival with a 15-day survival rate of all rats in the treatment group and also had a synergistic effect on the NDS, with a median neurological deficit score 72 hours after resuscitation of 12 as compared to an NDS of 31 with ethanol alone or 30 with vasopressin alone.

The administration of 2.0 g/kg of ethanol, 0.75 U/kg of vasopressin, 1 mg/kg lidocaine, 150 mg/kg of N-acetylcysteine, 0.25 U/kg insulin, 0.25 mg/kg folate, and 5 mg/kg thiamine provided nearly complete neuroprotection in the rat model of asphyxial cardiac arrest that was evident 7 days after resuscitation. Similarly, the administration of a multidrug combination comprising 2.0 g/kg of ethanol, 0.75 U/kg of vasopressin, 1 mg/kg lidocaine, and 300 mg/kg of N-acetylcysteine, as well as a multidrug combination comprising 2.0 g/kg of ethanol, 0.75 U/kg of vasopressin, 1 mg/kg lidocaine, and 0.25 U/kg insulin afforded nearly complete neuroprotection at 7 days post-resuscitation in the same model.

TABLE 1

Survival and neurological deficit scores (NDS) in an asphyxial cardiac arrest rat model.

| Intervention | Rats in protocol | Survival days | NDS day 3 | NDS day 7 |
| --- | --- | --- | --- | --- |
| Normothermia | 5 | 1, 1, 1, 1, 15 | NA, NA, NA, NA, 40 | NA, NA, NA, NA, 38 |
| Forced Hypothermia | 6 | 2, 2, 4, 1, 15, 15 | NA, NA, 45, 41, 40 | NA, NA, NA, NA, 40, 36 |
| Regulated Hypothermic Compound (Normothermic Conditions) | | | | |
| Ethanol (E) 0.5 g/kg | 3 | 1, 1, 1 | NA, NA, NA | NA, NA, NA |
| Ethanol 0.8 g/kg | 1 | 1 | NA | NA |
| Ethanol 1 g/kg | 2 | 1, 2 | NA, NA | NA, NA |
| Ethanol 1.5 g/kg | 3 | 2, 3, 4 | NA, 32, 41 | NA, NA, NA |
| Ethanol 2 g/kg | 3 | 4, 3, 3 | 31, 40, 30 | NA, NA, NA |

TABLE 1-continued

Survival and neurological deficit scores (NDS) in an asphyxial cardiac arrest rat model.

| Intervention | Rats in protocol | Survival days | NDS day 3 | NDS day 7 |
|---|---|---|---|---|
| Ethanol 2.5 g/kg | 2 | 1, 1 | NA, NA | NA, NA |
| Ethanol 3 g/kg | 2 | 1, 1 | NA, NA | NA, NA |
| Vasoactive Compound (Normothermic Conditions) | | | | |
| Dopamine 20 mcg/kg | 1 | 1 | NA | NA |
| Epinephrine 0.005 mg/kg | 1 | 1 | NA | NA |
| Epinephrine 0.01 mg/kg | 2 | 1, 1 | NA, NA | NA, NA |
| Milrinone 0.3 mg/kg | 2 | 1, 1 (epi/mil) | NA, NA | NA, NA |
| Vasopressin (V) 0.1 U/kg | 2 | 1, 1 | NA, NA | NA, NA |
| Vasopressin 0.5 U/kg | 3 | 3, 5, 7 | 37, 5, 36 | NA, NA, 22 |
| Vasopressin 0.75 U/kg | 2 | 3, 3 | 30, 30 | NA, NA |
| Anti-Arrhythmic Compound (Normothermic Conditions) | | | | |
| Lidocaine (L) 1 mg/kg | 1 | 1 | NA | NA |
| Anti-Oxidant (Normothermic Conditions) | | | | |
| N-Acetylcysteine (N) 50 mg/kg | 2 | 2, 1 | NA, NA | NA, NA |
| N-Acetylcysteine 150 mg/kg | 3 | 4, 3, 5 | 39, 34, 38 | NA, NA, NA |
| N-Acetylcysteine 300 mg/kg | 2 | 2, 3 | NA, 40 | NA, NA |
| Antihyperglycemic Compound (Normothermic Conditions) | | | | |
| Insulin (I) 0.25 U/kg | 1 | 2 | NA | NA |
| Vitamin (Normothermic Conditions) | | | | |
| Folate 0.25 mg/kg + Thiamine 5 mg/kg (FT) | 1 | 1 | NA | NA |
| Combination Therapy | | | | |
| (E)1.5 + (V)0.1 | 2 | 6, 7 | 15, 30 | NA, 34 |
| (E)2.0 + (V)0.1 | 2 | 15, 15 | 30, 35 | 32, 6 |
| (E)2.0 + (V)0.5 | 3 | 15, 15, 15 | 23, 27, 31 | 7, 7, 5 |
| (E)2.0 + (V)0.75 | 4 | 15, 15, 15, 15 | 22, 10, 14, 10 | 6, 7, 5, 5 |
| (E)2.0 + (V)0.75 + (L)1 | 3 | 15, 15, 15 | 6, 9, 11 | 5, 5, 2 |
| (E)2.0 + (V)0.75 + (L)1 + (N)50 | 2 | 15, 15 | 8, 7 | 3, 3 |
| (E)2.0 + (V)0.75 + (L)1 + (N)150 | 4 | 15, 15, 15, 15 | 5, 5, 6, 5 | 2, 3, 4, 4 |
| (E)2.0 + (V)0.75 + (L)1 + (N)300 | 2 | 15, 15 | 9, 20 | 1, 0 |
| (E)2.0 + (V)0.75 + (L)1 + (N)150 + (I)0.25 | 4 | 15, 15, 15, 15 | 5, 5, 4, 3 | 1, 0, 2, 2 |
| (E)2.0 + (V)0.75 + (L)1 + (N)150 + (I)0.25 + (FT)0.25/5 | 4 | 15, 15, 15, 15 | 2, 4, 6, 2 | 0, 0, 0, 0 |

TABLE 2

Summary of survival and neurological deficit scores (NDS) in an asphyxial cardiac arrest rat model.

| Intervention | Number of rats in protocol | Average Survival days | NDS day 3 | NDS day 7 |
|---|---|---|---|---|
| Normothermia | 5 | 3.8* | NA, NA, NA, NA, 40* | NA, NA, NA, NA, (38)* |
| Forced Hypothermia | 6 | 6.5 | NA, NA, 45, 41, 40(41) | NA, NA, NA, NA, (38) |
| Regulated Hypothermic Compound (Normothermic Conditions) | | | | |
| Ethanol (E) 0.5 g/kg | 3 | 1 | NA, NA, NA | NA, NA, NA |
| Ethanol 0.8 g/kg | 1 | 1 | NA | NA |
| Ethanol 1 g/kg | 2 | 1.5 | NA, NA | NA, NA |
| Ethanol 1.5 g/kg | 3 | 3 | NA, (36.5) | NA, NA, NA |
| Ethanol 2 g/kg | 3 | 3.33 | (31) | NA, NA, NA |

TABLE 2-continued

Summary of survival and neurological deficit scores (NDS) in an asphyxial cardiac arrest rat model.

| Intervention | Number of rats in protocol | Average Survival days | NDS day 3 | NDS day 7 |
|---|---|---|---|---|
| Ethanol 2.5 g/kg | 2 | 1 | NA, NA | NA, NA |
| Ethanol 3 g/kg | 2 | 1 | NA, NA | NA, NA |
| *Vasoactive Compound (Normothermic Conditions)* | | | | |
| Dopamine 20 mcg/kg | 1 | 1 | NA | NA |
| Epinephrine 0.005 mg/kg | 1 | 1 | NA | NA |
| Epinephrine 0.01 mg/kg | 2 | 1 | NA, NA | NA, NA |
| Milrinone 0.3 mg/kg | 2 | 1 | NA, NA | NA, NA |
| Vasopressin (V) 0.1 U/kg | 2 | 1, 1 | NA, NA | NA, NA |
| Vasopressin 0.5 U/kg | 3 | 5 | (36) | NA, NA, 22 |
| Vasopressin 0.75 U/kg | 2 | 3 | (30) | NA, NA |
| *Anti-Arrhythmic Compound (Normothermic Conditions)* | | | | |
| Lidocaine (L) 1 mg/kg | 1 | 1 | NA | NA |
| *Anti-Oxidant (Normothermic Conditions)* | | | | |
| N-Acetylcysteine (N) 50 mg/kg | 2 | 1.5 | NA, NA | NA, NA |
| N-Acetylcysteine 150 mg/kg | 3 | 3 | (38) | NA, NA, NA |
| N-Acetylcysteine 300 mg/kg | 2 | 2.5 | NA, (40) | NA, NA |
| *Antihyperglycemic Compound (Normothermic Conditions)* | | | | |
| Insulin (I) 0.25 U/kg | 1 | 2 | NA | NA |
| *Vitamin (Normothermic Conditions)* | | | | |
| Folate 0.25 mg/kg + Thiamine 5 mg/kg (FT) | 1 | 1 | NA | NA |
| *Combination Therapy* | | | | |
| (E) 1.5 + (V) 0.1 | 2 | 6.5 | (22.5) | NA, (34) |
| (E) 2.0 + (V) 0.1 | 2 | 15 | (32.5) | (19) |
| (E) 2.0 + (V) 0.5 | 3 | 15 | (27) | (7) |
| (E) 2.0 + (V) 0.75 | 4 | 15 | (12) | (5.5) |
| (E) 2.0 + (V) 0.75 + (L) 1 | 3 | 15 | (9) | (5) |
| (E) 2.0 + (V) 0.75 + (L) 1 + (N) 50 | 2 | 15 | (7.5) | (3) |
| (E) 2.0 + (V) 0.75 + (L) 1 + (N) 150 | 4 | 15 | (5) | (3.5) |
| (E) 2.0 + (V) 0.75 + (L) 1 + (N) 300 | 2 | 15 | (14.5) | (0.5) |
| (E) 2.0 + (V) 0.75 + (L) 1 + (N) 150 + (I) 0.25 | 4 | 15 | (4.5) | (1.5) |
| (E) 2.0 + (V) 0.75 + (L) 1 + (N) 150 + (I) 0.25 + (FT) 0.25/5 | 4 | 15 | (3) | (0) |

*0.5 U/kg vasopressin added; ( ): median neurological deficit score

The treated rats were tested in the Morris Water Maze at days 11, 12, 13, 14, and 15 after ROSC. The raw performance data and 15-day survival of the rats are presented in Table 3 and this data is summarized in Table 4.

In the rat model of asphyxial cardiac arrest, the administration of ethanol alone under normothermic conditions resulted in a mild reduction in mortality, and vasopressin alone under normothermic conditions had a minimal effect on mortality or the neurological deficit score (NDS). In contrast to the mild effects of either compound alone, the combination of ethanol and vasopressin, when allowed to become hypothermic, synergistically improved survival and reduced neurological deficits.

TABLE 3

Performance of rats in Morris Water Maze after asphyxial cardiac arrest and administration of various drugs.

| Intervention | 15 day survival | D11 | D12 | D13 | D14 | D15 |
|---|---|---|---|---|---|---|
| Normothermia | 1 | 120 | 120 | 120 | 120 | 120 |
| Forced Hypothermia | 2 | 120, 120 | 120, 120 | 110, 120 | 120, 120 | 120, 120 |
| (E)1.5 + (V)0.1 | 0 | | | | | |
| (E)2.0 + (V)0.1 | 2 | 120, 120 | 120, 120 | 118, 114 | 120, 110 | 108, 99 |
| (E)2.0 + (V)0.5 | 3 | 120, 120, 120 | 110, 112, 116 | 102, 100, 96 | 89, 75, 84 | 83, 80, 76 |
| (E)2.0 + (V)0.75 | 4 | 120, 120, 118, 120 | 120, 99, 102, 120 | 116, 84, 88, 107 | 100, 73, 69, 100 | 94, 59, 58, 106 |
| (E)2.0 + (V)0.75 + (L)1 | 3 | 120, 120, 120 | 112, 92, 120 | 99, 88, 118 | 84, 73, 120 | 80, 70, 100 |

TABLE 3-continued

Performance of rats in Morris Water Maze after asphyxial cardiac arrest and administration of various drugs.

| Intervention | 15 day survival | D11 | D12 | D13 | D14 | D15 |
|---|---|---|---|---|---|---|
| (E)2.0 + (V) 0.75 + (L)1 + (N) 50 | 2 | 120, 120 | 116, 114 | 107, 100 | 92, 90 | 88, 82 |
| (E)2.0 + (V) 0.75 + (L)1 + (N) 150 | 4 | 116, 120, 118, 116 | 84, 88, 84, 89 | 42, 60, 64, 57 | 28, 42, 38, 38 | 19, 29, 27, 30 |
| (E)2.0 + (V) 0.75 + (L) 1 + (N) 300 | 2 | 114, 100 | 84, 76 | 51, 38 | 36, 22 | 28, 12 |
| (E) 2.0 + (V) 0.75 + (L) 1 + (N) 150 + (I) 0.25 | 4 | 118, 120, 120, 110 | 92, 94, 92, 74 | 64, 56, 45, 39 | 24, 31, 26, 26 | 10, 14, 14, 16 |
| (E) 2.0 + (V) 0.75 + (L) 1 + (N) 150 + (I) 0.25 + (FT) 0.25/5 | 4 | 110, 118, 120, 115 | 88, 88, 90, 84 | 40, 48, 52, 44 | 22, 30, 28, 32 | 8, 18, 14, 16 |

E = ethanol in g/kg;
V = vasopressin in U/kg;
L = lidocaine in mg/kg;
N = N-acetylcysteine in mg/kg;
I = insulin in U/kg;
FT = folate and thiamine in mg/kg

TABLE 4

Average performance of rats in Morris Water Maze after asphyxial cardiac arrest and administration of various drugs.

| Intervention | 15 day survival | D11 | D12 | D13 | D14 | D15 |
|---|---|---|---|---|---|---|
| Normothermia | 1 | 120 | 120 | 120 | 120 | 120 |
| Forced Hypothermia | 2 | 120 | 120 | 115 | 120 | 120, 120 |
| (E) 1.5 + (V) 0.1 | 0 | | | | | |
| (E) 2.0 + (V) 0.1 | 2 | 120 | 120 | 116 | 115 | 104 |
| (E) 2.0 + (V) 0.5 | 3 | 120 | 113 | 93 | 83 | 80 |
| (E) 2.0 + (V) 0.75 | 4 | 120 | 110 | 99 | 86 | 79 |
| (E) 2.0 + (V) 0.75 + (L) 1 | 3 | 120 | 108 | 102 | 92 | 83 |
| (E) 2.0 + (V) 0.75 + (L)1 + (N) 50 | 2 | 120 | 115 | 104 | 91 | 85 |
| (E) 2.0 + (V) 0.75 + (L) 1 + (N) 150 | 4 | 118 | 86 | 56 | 36 | 27 |
| (E) 2.0 + (V) 0.75 + (L) 1 + (N) 300 | 2 | 112 | 80 | 45 | 29 | 20 |
| (E) 2.0 + (V) 0.75 + (L) 1 + (N) 150 + (I) 0.25 | 4 | 117 | 88 | 51 | 27 | 14 |
| (E) 2.0 + (V) 0.75 + (L) 1 + (N) 150 + (I) 0.25 + (FT) 0.25/5 | 4 | 116 | 88 | 46 | 28 | 14 |

E = ethanol in g/kg;
V = vasopressin in U/kg;
L = lidocaine in mg/kg;
N = N-acetylcysteine in mg/kg;
I = insulin in U/kg;
FT = folate and thiamine in mg/kg These data indicate that the induction of hypothermic temperatures afforded by the ethanol-comprising multidrug combinations used in these studies lead to enhanced survival and neuroprotection in a rodent model of asphyxial cardiac arrest. Neurons are very sensitive to ischemia and other types of damage. The demonstration that compositions comprising regulated hypothermic compounds are effective in protecting neurons from cell death during ischemia indicates that compositions comprising regulated hypothermic compounds can also be used to protect all types of cells throughout the body from damage due to ischemia or other types of clinical insults.

Example 3

Rats Receiving Bolus Followed by Slow Infusion Time to Target Temperature

Non-ischemic rats were administered normal saline at room temperature (30 ml/kg at 60 ml/kg/hr×30 minutes, followed by 6 ml/kg/hr (group 1), administered iced saline (30 ml/kg followed by iced saline at 6 ml/kg/hr) and external cooling (at completion of rapid infusion) to simulate forced hypothermia (group 2), a first composition containing ethanol 63 g/L (group 3); a second composition containing ethanol 63 g/L and vasopressin 2.7 U/L (group 4); and a third composition containing ethanol 63 g/L, 2.7 U/L vasopressin, and 66.0 mg/L lidocaine (group 5). The compositions were administered in an intravenous bolus or rapid infusion at a rate of 60 ml/kg/hr for 30 minutes followed by a slow infusion of 6 ml/kg/hr for 12 hours. Experiments in all groups except the forced hypothermia group were conducted at room (21° C.) temperature. Group 5 containing 63 g/L ethanol, 2.7 U/L vasopressin, and 66.0 mg/L lidocaine showed a steep decrease in temperature about 2° C. below baseline in about 42 minutes, 3° C. below baseline at 106 minutes and 4° C. below baseline about 125 minutes after initiation of the infusion. Groups 1-4 displayed less than a 1° C. decrease from baseline throughout the 24 hr experiment.

Example 4

Neurological Deficit Scores (NDS)

Following asphyxial cardiac arrest and resuscitation, rats were subjected to forced hypothermia (group 1) as described above or to regulated hypothermia by receiving a bolus followed by slow infusion as described above. The compositions for the bolus followed by slow infusion were a first composition containing ethanol 63 g/L, 2.7 U/L vasopressin, and 66.0 mg/L lidocaine (group 2); a second composition containing ethanol 63 g/L, 2.7 U/L vasopressin, and odansetron 4.6 mg/L (group 3); or a third composition containing 16.7 mg/L 7-OH-DPAT, 2.7 U/L vasopressin, and 66.0 mg/L lidocaine (group 4). Neurological deficit scores (NDS) were obtained after resuscitation from cardiac arrest. For days 1-3 following resuscitation from cardiac arrest, groups 2, 3, and 4 showed the least neurological damage as compared to the forced hypothermia group 1 or to a normothermic control group. The results indicate that the three compositions are able to protect the brain from injury using the methods of the invention.

Other results indicate that spraying the rat with water (simulating sweating) after administering the compositions of the invention markedly accelerates the cooling time to target temperature. The multidrug combinations of the invention will cool in environments ranging from 0° C. to about 25° C. However, the cooling effect can be accelerated by dropping the room temperature.

Example 5

Ethanol-Comprising Multidrug Combination Therapy Reduces Shivering

Rats are exposed to 80 minutes of surgery with titrated isoflurane anesthesia. A core temperature probe is implanted in the abdomen, a femoral vein cannula is externalized, and an EMG (electromylogram) lead is inserted into the mid-back muscle region. This phase of the protocol simulates an operation experienced by human subjects receiving general anesthesia.

Rats are then placed in a 30° C. high oxygen incubator for 210 minutes to regain temperature regulation while isoflurane dissipates. This phase of the protocol simulates conditions in a recovery room.

2 g/kg ethanol, 2 U/kg vasopressin, 2 mg/kg lidocaine, and 90 mg/kg N-acetylcysteine are administered intravenously over a 30-minute period starting 80 minutes prior to entering the shiver chamber. A control group receives normal saline (0.9%) at room temperature (e.g., about 20° C. to about 25° C.) in a volume and at a rate that matches the regulated hypothermia group.

After the recovery room, rats are moved to the shiver chamber for 60 minutes (with an environmental temperature of about 18° C.). The shiver chamber simulates environmental conditions when patients are moved from the recovery room to a regular hospital floor bed and this is when patients often shiver.

Rats are observed for an additional 60 minutes at 21° C. and then the experiment is concluded. Shivering is defined as a 50% increase in amplitude (milliVolts) from baseline EMG activity. A visual scale of shivering is also performed by an observer blinded to treatment (0=no shivering; 1=mild shivering; 2=moderate shivering; and 3=severe shivering).

Rats treated with forced hypothermia (n=4) received normal saline (0.9%) and rats that underwent regulated hypothermia (n=4) were infused with 2 g/kg ethanol, 2 U/kg vasopressin, 2 mg/kg lidocaine, and 92 mg/kg N-acetylcysteine. The electromyogram (EMG) activity of the rats was measured in the shiver chamber. The increased amplitude of electrical activity in the forced hypothermic group correlated with shivering (Fischer exact test p<0.05). All rats (4/4) in the forced hypothermia group shivered, while no rats (0/4) in the regulated hypothermia group shivered (Chi-square test p<0.05). Therefore, the administration of the multidrug combination therapy prevents shivering in a rat when exposed to reduced environmental temperatures.

Example 6

Preparation of Combination Therapies for Rapid Infusion Followed by Slow Infusion

TABLE 5

| E8V0.08L2 | Units | Total bolus dose (units/kg) | Total drug | Volume of each (ml) | Concentration |
|---|---|---|---|---|---|
| etoh | g | 1.89 | 0.57 | 7.783 | 63 g/L = 8% |
| vasopressin | Units | 0.08 | 0.0240 | 0.480 | 2.7 U/L |
| lidocaine | mg | 2 | 0.60 | 0.300 | 66.7 mg/L |
| Total vol (by adding NS) | | | | 9.0 | | ethanol 1.89 g/kg, vasopressin 0.08 U/kg, lidocaine 2 mg/kg (E8V0.08L2)

The table indicates how a syringe is prepared for delivery to a 300 g rat.

The Total bolus dose is the total bolus or concentration of compound during rapid infusion delivered to a rat (mg or U/kg depending on drug).

Bolus=30 ml/kg.

Rate of bolus 60 ml/kg/hr.

The bolus is started 5 minutes after resuscitation (ROSC) and was completed 35 min after ROSC.

The subsequent infusion began immediately after the bolus or rapid infusion was completed.

Rate of infusion was 6 ml/kg/hr.

Duration of infusion was for 12 hrs.

Total Infused Dose:

ethanol 4.53 g/kg, vasopressin 0.19 U/kg, lidocaine 4.8 mg/kg

TABLE 6

| E7V0.08L2 | Units | Total bolus dose (units/kg) | Units needed | Volume of each (ml) | Concentration |
|---|---|---|---|---|---|
| etoh | g | 1.66 | 0.50 | 7.835 | 55 g/L = 7% |
| vasopressin | Units | 0.08 | 0.0242 | 0.483 | 2.7 U/L |
| lidocaine | mg | 2 | 0.60 | 0.302 | 66.0 mg/L |
| Total vol (by adding NS) | | | | 9.09 | | ethanol 1.66 g/kg, vasopressin 0.08 U/kg, lidocaine 2 mg/kg (E7V0.08L2)

The table indicats how a syringe is prepared for delivery to a 302 g rat.

The total bolus dose is the total drug delivered to a rat (mg or U/kg depending on drug).

Bolus=30 ml/kg.

Rate of bolus 60 ml/kg/hr.

The bolus is started 5 minutes after resuscitation (ROSC) and was completed 35 min after ROSC.

The subsequent infusion began immediately after the bolus or rapid infusion was completed.

TABLE 7 ethanol 1.89 g/kg, vasopressin 0.08 U/kg, odansetron 0.138 g/kg (E8V0.08Od0.138)

| E8V0.08Od0.138 | Units | Total bolus dose (units/kg) | Total drug | Volume of each (ml) | Concentration |
|---|---|---|---|---|---|
| etoh | g | 1.89 | 0.52 | 7.083 | 63 g/L = 8% |
| vasopressin | Units | 0.08 | 0.0218 | 0.437 | 2.7 U/L |
| odansetron | mg | 0.138 | 0.038 | 0.377 | 4.6 mg/L |
| Total vol (by adding NS) | | | | 8.19 | |

Bolus=30 ml/kg.

Rate of bolus 60 ml/kg/hr.

The bolus is started 5 minutes after resuscitation (ROSC) and was completed 35 min after ROSC.

The subsequent infusion began immediately after the bolus or rapid infusion was completed.

Rate of infusion was 6 ml/kg/hr.

Duration of infusion was for 12 hrs.

Total Infused Dose:

ethanol 3.94 g/kg, vasopressin 0.19 U/kg, odansetron 0.33 mg/kg

TABLE 8

7-OH-DPAT 0.5 mg/kg, vasopressin 0.08 U/kg, lidocaine 2 mg/kg (D0.5V0.08L2)

| D0.5V0.08L2 | Units | Total bolus dose (units/kg) | Units needed | Volume of each (ml) | Concentration |
|---|---|---|---|---|---|
| 7-OH-DPAT | mg | 0.05 | 0.1260 | 6.538 | 16.7 mg/L |
| vasopressin | Units | 0.08 | 0.0202 | 0.403 | 2.7 U/L |
| lidocaine | mg | 2 | 0.50 | 0.252 | 66.0 mg/L |
| Total vol (by adding NS) | | | | 7.56 | |

Bolus=30 ml/kg.

Rate of bolus 60 ml/kg/hr.

The bolus is started 5 minutes after resuscitation (ROSC) and was completed 35 min after ROSC.

The subsequent infusion began immediately after the bolus or rapid infusion was completed.

Rate of infusion was 6 ml/kg/hr.

Duration of infusion was for 12 hrs.

Total Infused Dose:

7-OH-DPAT 1.2 mg/kg, vasopressin 0.19 U/kg, lidocaine 4.8 mg/kg.

TABLE 9

Molecular weights for calculating molarity

| | |
|---|---|
| Ethanol | 46.07 g/mol |
| Lidocaine | 234.34 g/mol |
| Odansetron | 293.36 g/mol |
| Vasopressin | 1084.25 g/mol |
| 7-OH-DPAT | 247.38 g/mol |
| Bromocriptine | 654.59 g/mol |

Example 7

Large Mammal Studies of Ethanol-Comprising Multidrug Combination Therapy

Fourteen anesthetized swine (N=7/group) were used in the protocol. Swine were intubated, mechanically ventilated, and an asphyxial cardiac arrest was induced by apnea from vecuronium and discontinuation of ventilation. Swine were resuscitated from 10 minutes of asphyxial cardiac arrest with mechanical ventilation, 100% oxygen, epinephrine, sodium bicarbonate and CPR using the ILCOR guidelines.

Swine in the forced hypothermia group (n=7 with vasopressin 0.08 U/kg and lidocaine 2 mg/kg) received peripheral administration of intravenous iced saline (5° C. 30 ml/kg) over 40 minutes starting five minutes after return of spontaneous circulation (ROSC). Swine in the regulated hypothermia group (n=7 ethanol 2 g/kg (63 g/L), vasopressin 0.08 U/kg (2.7 U/L) and lidocaine 2 mg/kg (66.7 mg/L), 30 ml/kg over 40 minutes at room temperature, starting 5 minutes after ROSC. When rapid infusions were complete, slow infusions containing the same solutions as the rapid infusion phase were administered at 5 ml/kg/hr and both groups were externally cooled (simulated hospital phase) with a circulating cool water blanket covering approximately 40% of the skin surface, to an esophageal temperature 4° C. (target temperature which relates to 33-34° C.) below baseline and then maintained at that target until 3 hours after resuscitation.

The time to reach therapeutic hypothermia was measured and compared between groups using a one way ANOVA with significance set at p<0.05. Secondary endpoints of serum and CSF NSE were also compared between groups.

The time to reach the target temperature was shorter with the regulated hypothermia group (93±6 minutes) compared to the forced hypothermia (172±16 minutes) group, with p≤0.001 (ANOVA). See FIG. 1. The shivering incidence was 0/7 in the regulated hypothermia group and 7/7 in the forced hypothermia group (CHI square p<0.01).

Blood and CSF levels of neuron specific enolase (NSE) were obtained as a screen of brain injury since NSE levels rise during reperfusion with brain injury (Auer et al. (2006) *Can J Emerg Med* 8:13-18; Tiainen et al. (2003) *Stroke* 34:2881-2886). The neuron specific enolase (NSE) levels are provided in Table 10. The lower NSE levels in the swine treated with regulated hypothermia (combination of ethanol, vasopressin, and lidocaine) in comparison to the swine that underwent forced hypothermia (iced saline with vasopressin and lidocaine) suggests that the ethanol-comprising multidrug combination is neuroprotective in large mammals.

TABLE 10

Neuron specific enolase (NSE) levels in swine following asphyxial cardiac arrest and forced or regulated hypothermia.

| | Base Serum | Serum 3 hr | CSF |
|---|---|---|---|
| Forced Hypothermia (n = 7) | | | |
| Mean | 0 | 6.0 | 49.7 |
| Std dev | | 1.6 | 32.6 |
| Regulated Hypothermia (n = 7) | | | |
| Mean | 0 | 0.7 | 17.3 |
| Std dev | | 1.9 | 1.9 |

The mean arterial pressure (MAP) and temperature changes (from the baseline temperature of about 37° C.) were measured, respectively, during the ten minutes of asphyxia and through 180 minutes following ROSC, during which forced hypothermia or regulated hypothermia was induced in the swine. The MAP of the forced hypothermia group administered iced solution (forced hypothermia: normal saline, 0.9%, vasopressin 0.08 U/kg and 2 mg/kg lidocaine at 5° C.) was compared to the regulated hypothermia group (regulated hypothermia: 2 g/kg ethanol, vasopressin 0.08 U/kg and 2 mg/kg lidocaine at room temperature). There was no significant difference in MAP between the two groups.

Blood glucose levels were also measured in both the forced and regulated hypothermia groups. During the first 10 minutes after cardiac arrest, the blood glucose level rose in both groups to about 280 mg/dl. After this initial rise, surprisingly, the blood glucose of the regulated hypothermia group dropped more rapidly and to a greater extent than the forced hypothermia group. By about 90 minutes after cardiac arrest, the blood glucose had returned to near normal levels in the regulated hypothermia group. The blood glucose levels in the forced hypothermia remained elevated.

Mean arterial pressure (MRP) was measured in both the forced and regulated hypothermia groups. At about 60 minutes after cardiac arrest, the swine in the regulated hypothermia group had a MRP of about 90 mmHg as compared to about 75 mmHg for the forced hyperthermia group. The pressure in the regulated hypothermia group gradually decreased and approached that of the forced hypothermia group by about 120 minutes following cardiac arrest.

Heart rate was measured in both the forced and regulated hypothermia groups during the experiment. There was no significant difference in beats per minute noted for the swine in the forced hypothermic and the regulated hypothermic groups.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of inhibiting, reducing, or reversing the damage due to an ischemic insult in a subject, said method comprising administering intravenously to said subject a therapeutically effective amount of a composition comprising ethanol, vasopressin, and lidocaine, wherein said composition is administered to induce regulated hypothermia in said subject, during or following said ischemic insult.

2. The method of claim 1, wherein said administering comprises administering the composition as a bolus, followed by administering the composition by a relatively slower infusion.

3. The method of claim 1, wherein said ischemic insult comprises a cerebral ischemic insult, a stroke, a cardiac arrest, asphyxia, a traumatic brain injury, a spinal cord injury, a near drowning, or an invasive or vascular surgery.

4. The method of claim 3, wherein said cardiac arrest is an asphyxial cardiac arrest, a ventricular cardiac arrest, or a hemorrhagic cardiac arrest.

5. The method of claim 2, wherein said bolus of the composition is administered as soon as possible after said ischemic insult.

6. The method of claim 2, wherein said bolus is administered at a rate of about 10 ml/kg/hr to about 80 ml/kg/h.

7. The method of claim 6, wherein said bolus is administered at a rate of about 60 ml/kg/h.

8. The method of claim 7, wherein said bolus is administered for about 30 minutes.

9. The method of claim 2, wherein about 0.75 g/kg to about 10 g/kg of ethanol is administered to said subject as a bolus.

10. The method of claim 9, wherein about 1.89 g/kg of ethanol is administered to said subject as a bolus.

11. The method of claim 2, wherein about 0.075 U/kg to about 2 U/kg of vasopressin is administered to said subject as a bolus.

12. The method of claim 11, wherein about 0.08 U/kg of vasopressin is administered to said subject as a bolus.

13. The method of claim 2, wherein about 1.0 mg/kg to about 4.0 mg/kg of lidocaine is administered to said subject as a bolus.

14. The method of claim 13, wherein about 2 mg/kg of lidocaine is administered to said subject as a bolus.

15. The method of claim 2, wherein about 0.75 g/kg to about 10 g/kg of ethanol, about 0.075 U/kg to about 2.0 U/kg of vasopressin, and about 1.0 mg/kg to about 4.0 mg/kg of lidocaine is administered to said subject as a bolus.

16. The method of claim 15, wherein about 1.89 g/kg of ethanol, about 0.08 U/kg of vasopressin, and about 2 mg/kg of lidocaine is administered to said subject as a bolus.

17. The method of claim 2, wherein said relatively slower infusion is at a rate of about 1 ml/kg/hr to about 9 ml/kg/hr.

18. The method of claim 17, wherein said relatively slower infusion is at a rate of about 1.5 ml/kg/hr.

19. The method of claim 18, wherein said relatively slower infusion is administered for about 4 to about 24 hours.

20. The method of claim 19, wherein said relatively slower infusion is administered for about 12 hours.

21. The method of claim 2, wherein about 1.0 g/kg of ethanol is administered to said subject during said relatively slower infusion.

22. The method of claim 2, wherein about 4.53 g/kg of ethanol is administered to said subject during said relatively slower infusion.

23. The method of claim 2, wherein about 0.19 U/kg of vasopressin is administered to said subject during said relatively slower infusion.

24. The method of claim 2, wherein about 4.8 mg/kg lidocaine is administered to said subject during said relatively slower infusion.

25. The method of claim 2, wherein about 4.53 g/kg of ethanol, about 0.19 U/kg of vasopressin, and about 4.8 mg/kg of lidocaine is administered to said subject during said relatively slower infusion.

26. The method of claim 2, wherein said composition has a concentration of ethanol of about about 63 g/L ethanol, a concentration of vasopressin of about 2.7 U/L vasopressin, and a concentration of lidocaine of about 66.7 mg/L of lidocaine.

* * * * *